United States Patent
Nuijens et al.

(10) Patent No.: US 6,333,311 B1
(45) Date of Patent: *Dec. 25, 2001

(54) USEFUL PROPERTIES OF HUMAN LACTOFERRIN AND VARIANTS THEREOF

(75) Inventors: Jan Nuijens, Heiloo; Patrick van Berkel, Delft, both of (NL)

(73) Assignee: Pharming, Leiden (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/017,043

(22) Filed: Feb. 2, 1998

Related U.S. Application Data

(60) Provisional application No. 60/036,859, filed on Feb. 3, 1997.

(51) Int. Cl.[7] .................................................. A61K 38/40
(52) U.S. Cl. .................................................. 514/12; 514/2
(58) Field of Search .................................................. 514/12.2

(56) References Cited

U.S. PATENT DOCUMENTS

| | | | |
|---|---|---|---|
| 5,849,885 | * | 2/1994 | Nuyens et al. |
| 5,861,491 | * | 10/1996 | Nuijens et al. |
| 5,919,913 | * | 2/1994 | Nuyens et al. |
| 6,066,469 | * | 9/1966 | Kruzel et al. |

FOREIGN PATENT DOCUMENTS

| | | | |
|---|---|---|---|
| 2183459 | * | 8/1995 | (CA). |
| 0 584 558 | | 3/1994 | (EP). |
| WO 92/21752 | | 12/1992 | (WO). |
| WO 93/22348 | | 11/1993 | (WO). |
| WO 97/45136 | | 12/1997 | (WO). |

OTHER PUBLICATIONS

Stites et al., Basic & Clinical Immunology, 8th ed., Appleton & Lange:Norwalk, CT, pp. 459 and 784.*

Elass–Rochard, E. et al., "Lactoferrin–Lipopolysaccharide interaction: involvement of the 28–34 loop region of human lactoferrin in the high–affinity binding to *Escherichia coli* 055B5 lipopolysaccharide" *Biochem. J.* 312:839–845 (1995).

Hutchens, T.W. et al., "Structurally intact (78–kDa) forms of maternal lactoferrin purified from urine of preterm infants fed human milk: Identification of a trypsin–like proteolytic cleavage event in vivo that does not result in fragment dissociation" *Proc. Natl. Acad. Sci. USA* 88:2994–2998 (Apr. 1991).

Mann, D.M. et al., "Delineation of the Glysosaminoglycan–binding Site in the Human Inflammatory Response Protein Lactoferrin" *J. Biol. Chem.* 269(38):23661–23667 (Sep. 23, 1994).

Miyazawa, K. et al., "Lactoferrin–Lipopolysaccharide Interactions" *J. Immunol.* 146(2):723–729 (Jan. 15, 1991).

Nuijens, J.H. et al., "Structure and Biological Actions of Lactoferrin" *J. Mammary Gland Biology and Neoplasia* 1(3):283–293 (1996).

van Berkel, P.H.C. et al., "Glycosylated and unglycosylated human lactoferrins both bind iron and show identical affinities toward human lysozyme and bacterial lipopolysaccharide, but differ in their susceptibilities towards tryptic proteolysis" *Biochem. J.* 312:107–114 (1995).

Wu, H.–f. et al., "Characterization of the Glycosaminoglycan–Binding Region of Lactoferrin" *Arch. Biochem. Biophys.* 317(1):85–92 (Feb. 20, 1995).

Ziere, G.J. et al., "Removal of 14 N–terminal Amino Acids of Lactoferrin Enhances its Affinity for Parenchymal Liver Cells and Potentiates the Inhibition of β–Very Low Density Lipoprotein Binding" *J. Biol. Chem.* 268(36):27069–27075 (Dec. 25, 1993).

Legrand, et al., "The N–Terminal Arg$^2$, Arg$^3$ and Arg$^4$ of Human Lactoferrin Interact with Sulphated Molecules But Not With the Receptor Present on Jurkat Human Lymphoblastic T–Cells", *Biochem J.*, 327(Pt. 3):841–846 (1997).

van Berkel et al., "N–Terminal Stretch Arg$^2$, Arg$^3$, Arg$^4$ and Arg$^5$ of Human Lactoferrin is Essential for Binding to Heparin, Bacterial Lipopolysaccharide, Human Lysozyme and DNA", *Biochem. J.*, 328(Pt. 1):145–151 (1997).

* cited by examiner

Primary Examiner—Claire M. Kaufman
(74) Attorney, Agent, or Firm—Townsend and Townsend and Crew LLP

(57) ABSTRACT

The invention provides compositions containing human lactoferrin, or lactoferrin variants deleted for one or more arginine residues in the amino-terminal region of the protein (i.e., in the first basic cluster), and methods of using the compositions. The human lactoferrin, or lactoferrin variants are useful for treatment of human diseases and conditions, including inflamation.

20 Claims, 15 Drawing Sheets

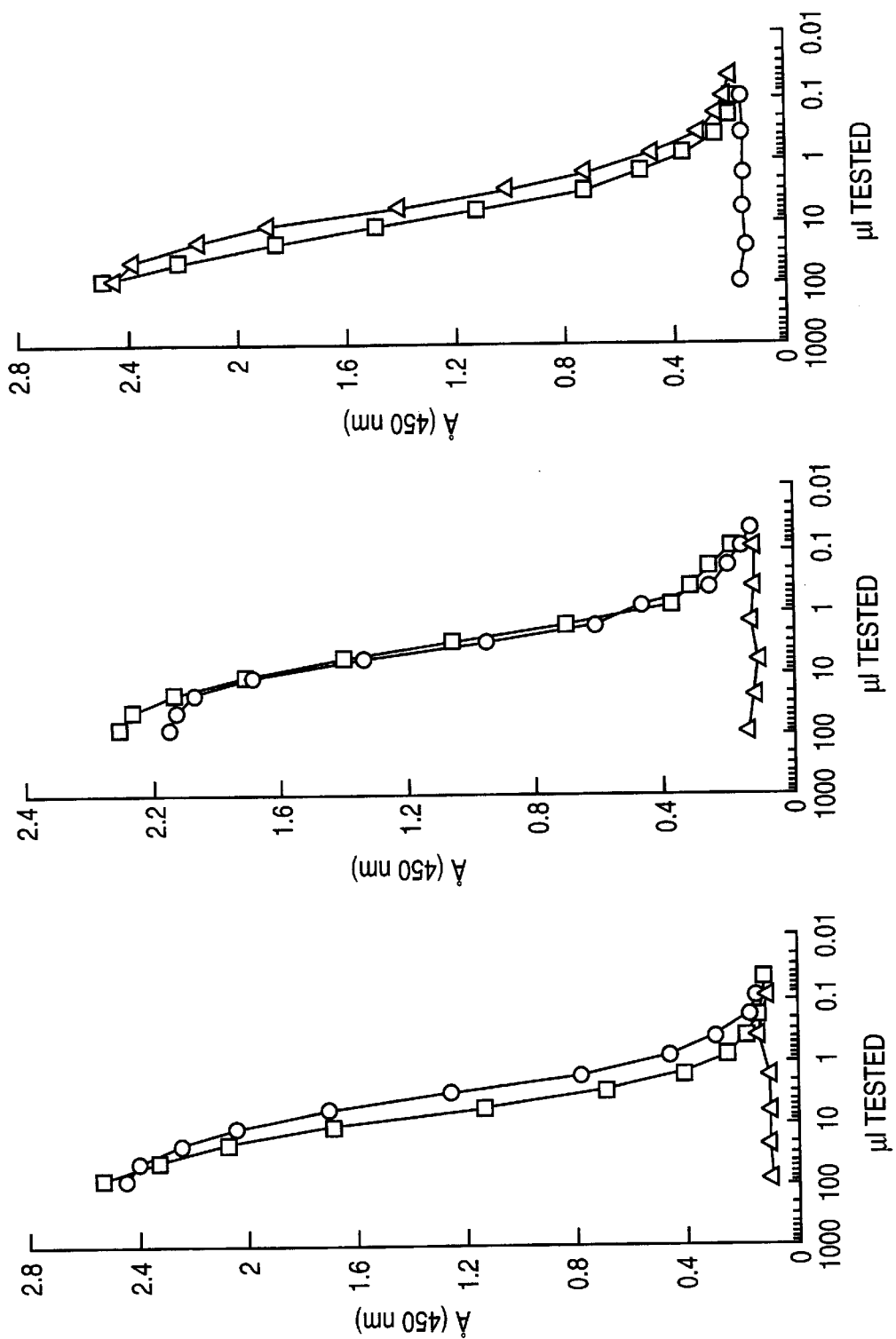

```
              1                    10                         20                    26
hLf  G R R R S V Q W C A V S N P E A T K C F Q W Q R N
bLf  A P R K N V R W C T I S Q P E W F K C R R W Q W R
mLf  K A T T V R W C A V S N S E E K C L R W Q N E 27              30                    40                         50   52
hLf  M R K V R G P P V S C L K R D S P I Q C I Q A I A E
bLf  M K K L G A P S I T C V R R A F A L E C I R A I A E
mLf  M R K V G G P P L S C V K S S T R Q C I Q A I V T
```

FIG. 13

USEFUL PROPERTIES OF HUMAN LACTOFERRIN AND VARIANTS THEREOF

This application claims the benefit of U.S. Provisional Application No. 60/036,859, filed Feb. 3, 1997, the disclosure of which is incorporated by reference.

BACKGROUND OF THE INVENTION

Lactoferrin (LF) is a metal binding glycoprotein of $M_r$ 77,000 found in milk, tears, saliva, bronchial, intestinal, vaginal and other secretions. LF is also present in the secondary granules of neutrophils. Lactoferrin plays an important role in numerous inflammatory and immune response functions such as regulation of monocyte colony stimulating factor synthesis, regulation of interleukin synthesis, activation of natural killer cell activity, inhibition of metastasis, and maturation of T-cells.

The amino acid sequence of LF has been determined by protein-sequencing and sequencing of cDNA clones. Human LF (hLF) consist of a polypeptide chain of 692 amino acids. The amino terminal region of hLF contains two clusters of basic residues, RRRR (SEQ ID NO:1) (residues 2–5) and RNMRKVR (SEQ ID NO:2) (residues 25–31). The LF polypeptide is folded into two globular lobes, each of which contains an iron-binding cleft. The high affinity of LF for iron confers to the protein certain antibacterial properties and, in addition, may play a role in the absorption of dietary iron by the small intestine.

Some of the biological activities of LF do not arise from the binding of iron but from its capacity to bind to other molecules. Direct intermolecular interactions between hLF and human lysozyme (hLZ) may explain the synergy between the antibacterial action of these two proteins. Interaction of hLF with bacterial outer membrane components such as lipopolysaccharide (LPS) and porins presumably plays an important role in the antimicrobial activity of hLF. Binding of hLF to the lipid A portion of LPS inhibits the LPS priming of neutrophils for enhanced fMLP-triggered superoxide release. Interaction of LF with heparin may account for the neutralization of the anticoagulant activity of heparin.

Some biological activities of LF arise from interactions between LF and cells via membrane bound receptors. For example, LF binding to specific receptors on monocytes, macrophages and activated lymphocytes results in inhibition of cytokine production. Cells that exhibit specific binding to hLF include liver cells, intestinal cells, mammary gland epithelial cells, monocytic cell lines, activated lymphocytes, and platelets.

BRIEF SUMMARY OF THE INVENTION

The invention provides compositions containing human lactoferrin, or lactoferrin variants deleted for one or more arginine residues in the amino-terminal region of the protein (i.e., in the first basic cluster), and uses of the compositions. In one aspect the invention is a composition containing a human lactoferrin variant deleted for one or more arginine residues in first basic cluster. The invention is particularly directed to the human lactoferrin variants $hLF^{-2N}$, $hLF^{-3N}$, $hLF^{-4N}$, and $hLF^{-5N}$. These binding properties of these variants differ in advantageous ways from those of natural lactoferrin. In one aspect, the composition is a pharmaceutical composition, optionally comprising bovine milk. In some embodiments, the human lactoferrin or lactoferrin variant is saturated with iron, typically at least 95% saturated.

The invention also relates to the uses of human lactoferrin and lactoferrin arginine-deletion variants. In one aspect, the invention provides methods for activating a lactoferrin receptor, for example the 105 kd lactoferrin receptor, by administering hLF or an hLF variant.

In another aspect, the invention provides a method for reducing or inhibiting release of a cytokine, such as IL-1, IL-2 or TNFα, from lactoferrin-receptor bearing cells in a patient, by administering lactoferrin or a lactoferrin variant.

In other aspects, the invention provides methods in which human lactoferrin or a lactoferrin variant is administered to a patient to inhibit myelopoieses, for treatment of a chronic inflammatory bowel disease, or to reduce TNFα-mediated neutrophil degranulation in a patient.

In another aspect, the invention provides a method for delivering iron to a lactoferrin-receptor-bearing cell in a patient by administering to the patient a composition of human lactoferrin or a lactoferrin variant which is at least about 95% saturated with iron. Administration of these compounds are beneficial, for example, in treatment of anemia or iron storage diseases.

In another aspect, the invention provides methods in which human lactoferrin or a lactoferrin variant is administered to a patient to reduce inflammation. Administration of hLF and hLF variants is useful for reducing reperfusion injury in a patient after myocardial infarction.

In other aspects, the invention provides methods in which human lactoferrin or a lactoferrin variant is administered to a patient to inhibit growth of a solid tumor in a patient and for stimulating natural killer (NK) cells in a patient.

The invention also provides methods for inhibiting entry into a cell of viruses, for example, CMV, HIV or HSV1 viruses, for which viral entry is mediated by an interaction between the virus and a cell surface proteoglycan.

In a related aspect, the invention is a composition containing human lactoferrin in which the first basic cluster of the lactoferrin is neutralized, for example, by the binding of an anti-lactoferrin monoclonal antibody or heparin, such that the lactoferrin binds a Jurkat cell 105 kD lactoferrin receptor with higher affinity than does natural lactoferrin.

In another aspect, the invention provides pharmaceutical compositions comprising a lactoferrin variant containing the first basic cluster, but not containing the second basic cluster.

BRIEF DESCRIPTION OF THE FIGURES

FIGS. 4A–4C show binding of the recombinant N- and C-lobe and natural hLF to anti-hLF mAbs. Serial dilutions of natural hLF (100 ng/ml, □) and conditioned medium of 293(S) cells secreting rN-lobe (○) or rC-lobe (Δ) were incubated with purified mAbs E11 (FIG. 4A); E3 (FIG. 4B) and E19 (FIG. 4C) coated to microtiter plates as described. Bound hLF was detected by subsequent incubation with peroxidase conjugated anti-hLF. The $A_{450}$ values measured after substrate conversion was stopped with sulfuric acid are indicated on the ordinate. The experimental volume (μl) tested is indicated on the abscissa.

FIG. 13 shows the N-terminal amino acid sequence alignment of hLf (SEQ ID NO:3), bLf (SEQ ID NO:4) and mLf (SEQ ID NO:5) showing the distribution of basic residues. Identical amino acids between hLf [Metz-Boutigue et al., 1984, Eur. J. Biochem. 145, 659–676; Rey et al., 1990, Nucleic Acids Res. 18, 5288], bLf [Pierce et al., 1991, Eur. J. Biochem. 196, 177–184] and mLf [Pentecost et al., 1987, J. Biol. Chem. 262, 10134–10139] are boxed. Arg and Lys residues are underlined in black and grey, respectively. Numbering of the sequence is according to Metz-Boutigue et al., supra.

DETAILED DESCRIPTION

I. Introduction

Figure 2:
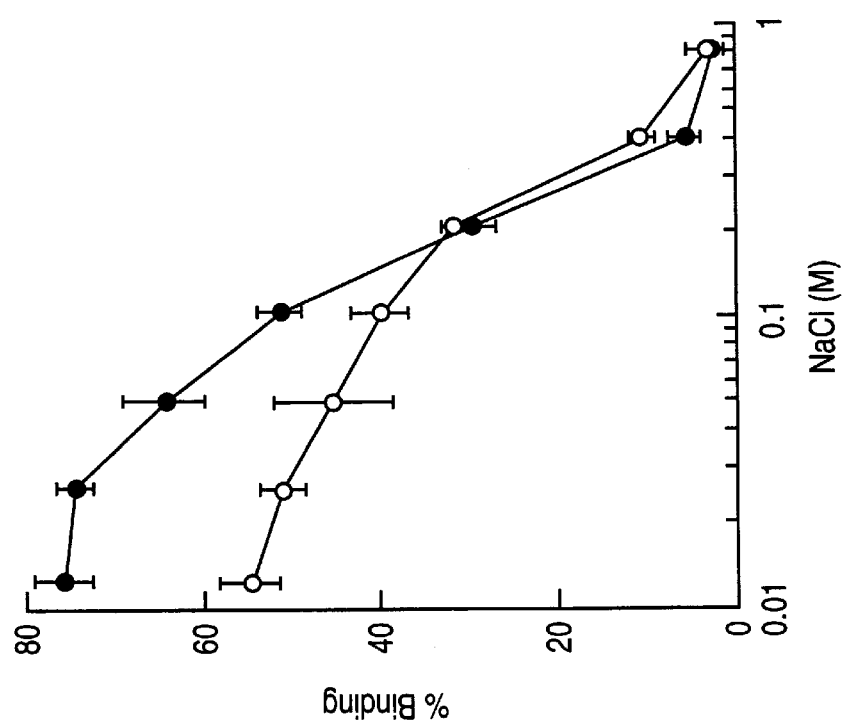
FIG. 2 shows the influence of NaCl concentration on the binding of hLF to LPS and hLZ. Equal amounts of Sepharose to which LPS from *Salmonella minnesota* Re595 (●) or hLZ (○) was immobilized, were suspended in 10 mM sodium phosphate buffer, pH 7.6 containing 0.02% (w/v) Tween-20 and varying concentrations of NaCl. Sepharose beads were incubated with $^{125}$I-hLF by head-over-head rotation. After 16 hours, the beads were washed with 10 mM sodium phosphate, 0.02% Tween-20, and bound radioactivity was measured. Results were expressed as percentage binding of the total amount of $^{125}$I-hLF added. The NaCl concentration of the Sepharose suspension is indicated on the abscissa.

The present invention provides lactoferrin variants having the biological activities of natural LF, e.g., binding to high affinity LF receptors on cells, but with reduced binding, relative to natural LF, to heparin, DNA, human lysozyme, the Lipid A component of bacterial lipopolysaccharide (LPS), and sulfated cell surface molecules. In particular, the invention provides variants lactoferrin of from which 1–4 arginine residues from the first basic cluster (i.e., residues 2–5) have been deleted.

The invention also provides methods of using hLF and LF variants for alleviation of certain diseases and conditions in humans and other animals. As is disclosed herein, human lactoferrin is useful for the treatment of, e.g., inflammation, anemia, myelopoieses and for reducing reperfusion injury, cytokine release, and proteoglycan-mediated entry of virus into cells. Lactoferrin variants are also useful for treatment of these diseases and conditions, and are especially useful for treatment of those conditions for which beneficial effects of natural lactoferrin treatment are due to binding to a high affinity LF receptor. Moreover, an advantage to the use of the LF variants is that the desired physiological effect can be achieved while avoiding side effects caused by the binding of natural LF to heparin, DNA, human lysozyme, Lipid A, or cell surface proteoglycans. For example, the lactoferrin variants of the invention may be used to deliver nutritional iron to cells, without concurrent neutralization of heparin and similar effects. Because the LF variants have little or no binding to sulfated cell surface molecules, and bind with increased affinity to high affinity LF receptors, more efficient targeting of LF to these receptors can be achieved.

II. Definitions

Natural Lactoferrin

As used herein, "natural lactoferrin" refers to a full-length human lactoferrin polypeptide that includes the N-terminal cluster of four consecutive arginine residues, e.g., a polypeptide having an amino acid sequence substantially as described by Metz-Boutigue et al., 1984, *Eur. J. Biochem.* 659:1451, noting the sequence inconsistencies identified in PCT publication WO91/08216 and other published protein and DNA sequences. The term natural lactoferrin also includes naturally occurring human allelic variants and amino acid sequence variants that have been modified by the insertion, substitution, or deletion of one or more amino acids as compared to a naturally occurring human lactoferrin, except that any variant with a deletion in the first basic cluster (i.e., amino-tenninal residues 2–5) and/or a deletion in the second basic cluster (i.e., residues 25–31) is not natural lactoferrin.

Natural lactoferrin includes recombinantly encoded human lactoferrin ("rhLF") expressed in a transgenic non-human animal, such as a bovine, where the glycosylation pattern may be distinct from glycosylation patterns of naturally occurring human lactofetrin obtained from human milk.

Lactoferrin Variant

The lactoferin variants described herein comprise polypeptides having the sequence of natural lactoferrin from which 1, 2, 3 or 4 arginine residues at the amino terminus have been removed (i.e., deletion of all or part of the first basic cluster) or from which the residues of the second basic cluster have been removed, or from which both the first and second basic clusters have been removed. The arginine residues of the first basic cluster can be removed by proteolysis of natural lactoferrin or by expression of a polynucleotide encoding a truncated hLF. Alternatively, one or more arginine residues of the first basic cluster can substituted for by other (i.e., other than arginine) amino acids, e.g., by directed mutagenesis of a polynucleotide encoding hLF. In preferred embodiments, the one or more arginine residues of the first basic cluster are deleted or mutated to an amino acid that is not positively charged at physiological pH, i.e., a neutral or acidic residue, usually to a neutral amino acid, most often alanine, leucine, glycine, valine or isoleucine. Hereinafter, reference to a hLF variant from which all or some of the arginine residues the first basic cluster have been "deleted" or "removed" refers both to removal of the arginines of the first basic cluster by deletion or by mutagenesis, unless it is explicitly stated otherwise.

The amino-terminal sequence of hLF is: N'-GRRRRSVQWC (SEQ ID NO:6). Lactoferrin variants of the invention include a variant having a deletion of one arginine (along with the terminal glycine) residue (referred to as $hLF^{-2N}$), a variant having two arginine residues removed (referred to as $hLF^{-3N}$), a variant having three arginine residues removed (referred to as $hLF^{-4N}$), and a variant having all four arginine residues removed (referred to as $hLF^{-5N}$).

Other lactoferrin variants are hLF from which the residues of the second basic cluster have been deleted or mutated (e.g., to uncharged residues). Still other lactoferrin variants of the invention have a deletion of the second basic cluster and deletions of one or more amino-terminal arginine residues.

Neutralized Lactoferrin

As used herein, "neutralized lactoferrin" is lactoferrin having substantially the sequence of native lactoferrin but that, by virtue of modification of the residues of the first basic cluster, is not able to bind to a LF ligand, e.g., heparin, as well as natural human lactoferrin, as measured by the solid phase ligand binding assay described in Example I, infra, but still binds 105 kd lactoferrin receptor found on Jurkat human lymphoblastic T-cells (Bi et al., 1994, *Eur. J. Cell Biol.* 65, 164–171 and Bi et al., 1996, *Eur. J. Cell Biol.* 69, 288–296) as measured by the cell binding assay described in Example II, infra. "Modification" includes chemical modification of the residues of the first basic cluster or, alternatively, binding of a molecule that blocks (i.e., through steric hinderance) the interaction of the first basic cluster of lactoferrin and heparin. Blocking molecules include monoclonal antibodies, fragments thereof, and LF ligands such as human lysozyme or heparin.

Substantially Free

An LF variant composition is substantially free of other human proteins (including natural hLF) when at least about 90%, more usually at least about 95%, and most commonly at least about 99% of the human protein present in the sample is the LF variant. The amount of any specific protein present in a sample can be determined by quantitative SDS-PAGE (for relatively simple mixtures) or by immunological assays (e.g., ELISA and RIA) for more complex mixtures (e.g., a mixture of bovine milk proteins and LF variant).

Immunological and molecular biological methods are well known and are described, for example, in Sambrook et al., Molecular Cloning—A Laboratory Manual, 2nd Ed., Cold Spring Harbor Laboratory, Cold Spring Harbor, N.Y., 1989 and Harlow and Lane, Antibodies: A Laboratory Manual, Cold Spring Harbor, N.Y. (1988), both of which are incorporated herein in their entirety and for all purposes.

Substantially Pure

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

III. Production of Lactoferrin and Lactoferrin Variants

LF variants lacking one or more of the amino terminal arginine residues may be produced by a variety of methods.

Preferred methods of production include (1) proteolytic cleavage of natural LF, or (2) recombinant expression, e.g., mutagenesis of a LF gene followed by expression in cells or transgenic animals of the LF variant, with recombinant expression most preferred. Deletion of the residues of the second basic cluster is preferably carried out by in vitro mutagenesis.

A. Purification and subsequent proteolytic cleavage of LF.

LF variants may be produced by cleavage of purified lactoferrin with a protease, preferably a serine protease and most preferably ttypsin. LF is abundant in milk and is most easily purified from this source, although it is also found in exocrine secretions and secondary granules of neutrophils. A preferred source of hLF is milk from a transgenic bovine species containing a human lactoferrin transgene. The transgene-encoded human lactoferrin is substantially purified from other milk proteins in the milk of transgenic cows, and is preferably substantially isolated from endogenous bovine lactoferrin, if present in the milk.

Numerous methods for purification of human lactoferrin from milk have been reported. See, for example, U.S. Pat. Nos. 4,436,658; 4,791,193; and 4,668,771, which are incorporated herein by reference. See also, Nuijens et al. *J.*, 1996, *Mammary Gland Biology and Neoplasia* 1:3, 283–293 (1996) and references cited therein.

A preferred method for hLF purification is described PCT Application PCT/EP95/00583, which is incorporated herein by reference. Briefly, milk or a milk fraction containing hLF is contacted with a strong cation exchange resin (e.g., S Sepharose™) in the presence of relatively high ionic strength (0.2M to 0.5M NaCl or KCl, preferably 0.4M NaCl or KCl) to prevent binding of non-lactoferrin proteins and other substances to the strong cation exchange resin and to reduce electrostatic interactions of lactoferrin with other proteins (e.g., caseins) or substances (e.g., lipopolysaccharide), and to liberate lactoferrin from complexes. The strong cation exchange resin containing the bound lactoferrin is separated from the unbound compounds in the milk or milk fraction, typically by centrifugation or sedimentation followed by batchwise washing and/or by pouring the resin into a column and washing the beads with buffer having approximately equal or lower salt concentration. The lactoferrin bound to the cation exchange resin is eluted with an aqueous, typically buffered, NaCl or KCl gradient (e.g., linear gradient of 0–1M NaCl in 20 mM sodium phosphate, pH 7.5) or by batch elution or stepwise elution with an aqueous, preferably buffered, NaCl or KCl solution of 0.4M or greater, preferably at least 0.5M NaCl or KCl. By selecting appropriate elution conditions, human lactoferrin may be substantially purified from bovine milk and substantially separated from bovine lactoferrin by an efficient method.

Human lactoferrin (e.g., rhLF) may be further purified from endogenous lactoferrin (e.g., bLF) by the additional subsequent step of rechromatography on a strong cation exchanger, such as S Sepharose™ Fast Flow, with salt gradient or stepwise elution to separate human lactoferrin from remaining traces of endogenous nonhuman lactoferrin species (e.g., bLF), and/or may optionally include affinity chromatography with a concanavalin A resin to further separate human lactoferrin from bLF, with bLF being more strongly bound to the Con A resin than hLF.

The tryptic digestion of purified natural lactoferrin may be carried out as follows: Five milligrams of native hLf are incubated with trypsin at an enzyme: substrate molar ratio of 1:8 at 37° C. in PBS. Digestion is stopped after 1, 5, 25 min and 3 h by the addition of a 12-fold molar excess of SBTI and N-terminal integrity is monitored, for example by analytical Mono S chromatography (Van Berkel et al., 1995, *Biochem. J.* 312: 107–114) and standard techniques such as SDS-PAGE, chromatography, and protein sequencing.

Following proteolysis, the LF variants may be separated from each other and from natural (i.e., uncleaved) hLF (and other proteins, if present) by cationic exchange chromatography (e.g., Mono S; heparin), Hydrophobic Interaction Chromatography (MIC) or Cibracon Blue Sepharose chromatography. In one embodiment, the LF variants are separated from uncleaved LF (and each other) by batch-wise incubation of recombinantly expressed lactoferrin or lactoferrin variants and S Sepharose for 4 h. The mixture is poured into a column and the lactoferrin eluted with 20 mM sodium phosphate, 0.5 M NaCl, pH 7.5. The S Sepharose eluate is diluted in 20 mM sodium phosphate, pH 7.5 (buffer A), applied on a Mono S HR 5/5 cation exchange column and eluted with a linear salt gradient of 0 to 0.5 M NaCl in 60 ml of buffer A at a flow rate of 0.5 ml/min. Natural hLF elutes at 0.7 M NaCl (Van Berkel et al., 1995, *Biochem J.* 312: 107–114) and $hLF^{-5N}$ elutes at about 0.33 M NaCl. The $hLF^{-3N}$ and $hLF^{-2N}$ species elute from Mono S at about 0.5 and about 0.6 M NaCl, respectively.

B. Mutagenesis and Expression of Recombinant hLF or hLF Variants

In vitro mutagenesis and expression of mutant proteins are well known and is described generally in Ausubel et al., *Current Protocols in Molecular Biology*, Greene Publishing and Wiley-Interscience, New York (1987) and in Sambrook et al., Molecular Cloning—A Laboratory Manual, 2nd Ed., Cold Spring Harbor Laboratory, Cold Spring Harbor, N.Y., 1989, both of which are incorporated herein by reference in their entirety and for all purposes. Also see, Kunkel, 1985, *Proc. Natl. Acad. Sci.* 82:488 (describing site directed mutagenesis) and Roberts et al., 1987, *Nature* 328:731–734) or (Wells, J. A., et al. (1985) *Gene* 34:315 (describing cassette mutagenesis).

Lactoferrin and lactoferrin variants can be expressed by cultured cells using well known recombinant techniques. Typically, nucleic acids encoding the desired polypeptides are used in expression vectors. The phrase "expression vector" generally refers to nucleotide sequences that are capable of affecting expression of a structural gene in hosts compatible with such sequences. These expression vectors typically include at least suitable promoter sequences and optionally, transcription termination signals. Additional factors necessary or helpfiul in effecting expression may also be used as described herein. DNA encoding the lactoferrin polypeptides of the present invention will typically be incorporated into DNA constructs capable of introduction into and expression in an in vitro cell culture. Often, the nucleic acids of the present invention may be used to produce a suitable recombinant host cell. Specifically, DNA constructs will be suitable for replication in a prokaryotic host, such as bacteria, e.g., *E. coli*, or may be introduced into a cultured mammalian, plant, insect, e.g., Sf9, yeast, fungi or other eukaryotic cell line. DNA constructs prepared for introduction into a particular host, e.g., insect or bacteria, will typically include a replication system recognized by the host, the intended DNA segment encoding the desired polypeptide, and transcriptional and translational initiation and termination regulatory sequences operably linked to the polypeptide encoding segment. A DNA segment is operably linked when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of the polypeptide. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof. The selection of an appropriate promoter sequence will generally depend upon the host cell selected for the expression of the DNA segment. Examples of suitable promoter sequences include prokaryotic, and eukaryotic promoters well known in the art. See, e.g., Sambrook et al., Molecular Cloning: A Laboratory Manual (2d ed.), vols. 1–3 Cold Spring Harbor Laboratory (1989). The transcriptional regulatory sequences will typically include a heterologous enhancer or promoter which is recognized by the host. The selection of an appropriate promoter will depend upon the host, but promoters such as the trp, lac and phage promoters, tRNA promoters and glycolytic enzyme promoters are known and available. See Sambrook et al., (1989).

Conveniently available expression vectors which include the replication system and transcriptional and translational regulatory sequences together with the insertion site for the polypeptide encoding segment may be employed. Examples of workable combinations of cell lines and expression vectors are described in Sambrook et al., and in Metzger et al., Nature 334:31–36 (1988). For example, suitable expression vectors may be expressed in, e.g., insect cells, e.g., Sf9 cells, mammalian cells, e.g., CHO cells and bacterial cells, e.g., E. coli.

In a preferred embodiment, the human lactoferrin and variants are produced by expression in transgenic animals (ie., non-human animals containing an exogenous DNA sequence in the genome of germline and somatic cells introduced by way of human intervention) such as bovines, goats, rabbits, sheep, pigs or mice. Methods for production of recombinant polypeptides by transgenic nonhuman species are known in the art and are described, for example, in U.S. Pat. Nos. 5,304,489; 5,633,076; and 5,565,362 which are incorporated herein by reference, as well as in PCT publications PCT/US93/05724 and PCT/US95/09580, both of which are incorporated herein by reference. An advantage of the transgenic animals is the isolation of LF in large amounts, especially by economical purification methods. For example, the production of transgenic bovine species containing a transgene encoding a human lactofeirin polypeptide targeted for expression in mammary secreting cells is described in WO91/08216, incorporated herein by reference. When lactoferrin variants are produced in transgenic bovines the human protein may be separated from the bovine milk proteins (e.g., whey proteins, caseins, bovine lactoferrin, IgA, albumin, lysozyme, β-lactoglobulin, etc.) before use (e.g., administration to patients). Alternatively, use may be made of whole or partially purified bovine milk containing the human lactoferrin protein or variant.

C. Alternative Methods for Neutralizing hLF Basic Clusters

Although deletion of the residues in the first or second basic cluster of hLF is a preferred method for generating a hLF with changed physiological properties, other methods for neutralizing one or both basic clusters exist. For example, the first basic cluster can be neutralized by incubating hLF with ligands such as heparin, which binds at the first cluster and inhibits binding of lactoferrin to the 105 kd lactoferrin receptor, LPS, human lysozyme, and other molecule for which binding is first-cluster dependent.

A preferred method for neutralizing the first basic cluster is to incubate hLF with a monoclonal antibody that binds at the amino terminus and prevents binding between the first basic cluster and a target molecule (e.g., heparin). Methods for producing monoclonal antibodies are well known (see, e.g., Goding et al., Monoclonal Antibodies: Principles and Practice (2d ed.) Acad. Press, N.Y., and Harlow and Lane, Antibodies: A Laboratory Manual, Cold Spring Harbor Laboratory, N.Y., 1988). Use of human or humanized monoclonal antibodies are most preferred because this reduces the possibility of an antigenic response following administration to a patient (see e.g., U.S. Pat. Nos. 5,569,825 and 5,585,089). Antigen-binding fragments of monoclonal antibodies, e.g., Fab, Fab' F(ab')$_2$, Fabc and Fv fragments, are similarly usefuil. It will be recognized that antibodies or antibody fragments can also be used for binding to the second basic cluster and preventing second-cluster dependent binding.

IV. Properties of Lactoferrin and Lactoferrin Variants

A. Binding to heparin, Lipid A, DNA and human lysozyme.

Natural hLF binds to heparin, Lipid A, DNA and human lysozyme (hLZ). One discovery of this invention is that LF variants lacking one, two or three arginines of the first basic cluster show a strong decrease in reactivity for each of these four ligands, and binding is undetectable in standard assays (e.g., solid phase ligand binding assays) when all four of the amino-terminal arginine residues are deleted.

The binding properties of natural LF and the LF variants can be measured in standard binding assays (see section 5.3.2, infra) and expressed in terms of reactivity where the level of binding of natural LF to a ligand is defined as 100% reactivity. The reactivity of the LF variants with the natural LF ligands heparin, DNA, Lipid A and hLZ is typically less than 80%, more usually less than 60%, often less than 15%. For some LH variants (e.g., those with a deletion of all four arginine residues from the first basic cluster) reactivity is undetectable.

B. Binding Assays

Assays suitable for measuring ligand-receptor interactions, such as the binding by natural LF and LF variants to heparin, lipid A, DNA, and human lysozyme, include assays solid-phase ligand binding assays and competitive solid-phase binding assays (see, e.g., Mann et al., 1994, J. Biol. Chem. 269:23661–67). In a preferred embodiment, the solid-phase binding assays as described in Example I, infra will be determined to measure binding by lactoferrin variants and natural LF. Typically, binding of the LF receptor by hLF or a hLF variant results in activation of the LF receptor. Methods for assaying receptor activation are known, for example, the resulting intracellular calcium shift can be measured (see, e.g., Misra et al., 1994, J. Biol. Chem. 269:18303–306).

C. Specific Binding to Cell Membrane Associated Receptors

Some of the biological activities of hLf are linked to its ability to strongly chelate iron, whereas other activities relate to the interaction of hLf with target cells, including intestinal cells (Hu et al., 1990, Biochemistry 29, 535–541; Kawakam et al, 1991, Am. J. Physiol. 261, G841–G846; Mikogami et al, 1994, Am. J. Physiol. 267, G308–G31), mammary gland epithelial cells (Rochard et al, 1992, Anticancer Res. 1, 2047–2052), hepatocytes (Regoeczi et al, 1985, Am. J. Physiol. 248, G8–G14; MacAbee et al, 1991, J. Biol. Chem. 226,23624–23631; Ziere et al, 1992, J. Biol. Chem. 267, 11229–11235), monocytes (Ismail et al, 1993, J. Biol. Chem. 268, 21618–21625), activated lymphocytes (Mazurier et al, 1989, Eur. J. Biochem. 179, 481–487) and platelets (Leveugle et al, 1993, *Eur. J. Biochem.*, 213, 1205–1211) each of which is incorporated by reference in their entirely and for all purposes.

LF binds to cell surfaces through two classes of LF binding sites: relatively low affinity sites which are cell surface sulfated molecules (e.g., cell surface proteoglycans or glycosaminoglycans) and high affinity receptors. In one aspect, the present invention is based, in part, on the discovery that binding to the low affinity sites is mediated by the first cluster of basic arginine residues, and deletion (or neutralization) of one or more of these residues reduces or eliminates binding to the low affinity sites. Thus, an hLF variant of the of the present invention will typically bind a high affinity LF receptor with an affinity of at least about 10 nM, usually between about 10 nM and about 40 nM. Cell binding assays are well known and are described in, e.g., Mazurier, 1989, *Eur. J. Biochem.* 179:481–87, as well as in Example II, infra. In contrast, deletion of one or more of the amino-terminal arginine residues does not reduce or abolish binding to the high affinity LF receptor.

High affinity LF binding sites have been found on activated lymphocytes, mammary gland epithelial cells, platelets, monocytes, macrophages, intestinal cells, and hepatocytes and are thought to exist on other cell types as well. A 105 kD specific hLf receptor has been characterized in activated lymphocytes (Mazurier et al., 1989, *Eur. J. Biochem.* 179, 481–487), the Jurkat T-cell line (Bi et al., 1994, *Eur. J. Cell Biol.* 65, 164–171; Bi et al., 1996, *Eur. J. Cell Biol.* 69,288–296) and platelets (Leveugle et al., 1993, *Eur. J. Biochem.*, 213,1205–1211).

Binding of LF to the 105 kD receptor has been shown to inhibit platelet aggregation and is likely involved in the growth factor and/or differentiation activities of hLF. This receptor has been localized in human lymphoblastic T-cells (ie., Jurkat cells, Pawelec et al., 1982, *Eur. J. Immuno.* 12:387–92) to the cell surface in coated pits vesicles as well as in intracellular vesicles. Internalization of hLF by Jurkat cells has been demonstrated. Jurkat cells may be obtained from the American Type Culture Collection [ATCC] located at 10801 University Boulevard, Manassas, Va. 20110-2209. LF binds to the lymphocyte (Jurkat cell) high affinity receptor with a kD of approximately 40 nM.

The 105 kD receptor can be identified by immunological methods. For example, a specific rabbit anti-105 kD receptor polyclonal antibody has been described. This, or a similar polyclonal antibody, or an anti-105 kD receptor monoclonal antibody, can be used to identify the receptor on other cell types. For example, the polyclonal antibody referred to supra has been found to bind to epithelial cells from non-malignant human breast, benigin mastopathics and breast carcinomas (Rochard et al., 1992, *Anticancer Research* 12: 2047–52). Alternatively, the 105 kD receptor can be identified by ligand blotting (see, e.g., Ausubel et al., Current Protocols in Molecular Biology, Greene Publishing and Wiley-Interscience, New York) using labeled hLF (or amino-terminally deleted hLF) and membrane protein preparations of cells.

A specific hLF receptor has been isolated from intestinal brush border membranes and has a reported $M_r$ of 110 (Kawaskami and Lonnerdal, 1991, *Am. J. Physiol.* 261:G841–46). It is likely, but has not yet been demonstrated, that this receptor is the same as, or closely related to, the 105 kD receptor.

In hepatocytes, LF binds to a chylomicron remnant receptor or the LDL-receptor-related protein (LRP) present on the cell surface. LF inhibits uptake of beta-VLDL containing chylomicron remnants. Lactoferrin binding to murine peritoneal macrophages apparently occurs via the Low density lipoprotein Receptor-related Protein (LRP), a member of the structurally related cell surface receptor family that mediates endocytosis of lipoproteins and other plasma proteins. The nature of hLF binding to monocytes and macrophages is incompletely characterized, although it is appears to be mediated, at least in part, a member of the LRP/chylomicron remnant receptor (Misra et al., 1994, *J. Biol. Chem.* 269:18303–306).

V. Pharmaceutical and Nutritional Applications

A. Indications

Lactoferrin exhibits a number of biological activities that provide benefit in a therapeutic setting. These include anti-inflammatory, anti-viral and anti-infective activities, as well a pro- and anti-coagulant effects, modulation of complement activation, inhibition of LPS mediated activation of neutrophils, regulation of transcription, growth promotion of intestinal epithelial cells, inhibition of hydroxyl-radical formation, and a role in intestinal iron uptake and excretion. Other properties and biological activities of lactoferrin are described in Nuijens et al., 1996, *J. Mammary Gland Biology and Neoplasia* 1:3,283–293, which is incorporated herein by reference in its entirety and for all purposes.

The human lactoferrin variants of the invention, and neutralized lactoferrin, have generally the same activities and uses as natural lactoferrin, except that deletion of the arginines of the first basic cluster results in reduction in binding to heparin, Lipid A, DNA, lysozyme, and cell surface sulfated molecules, as described in the Examples, infra. Thus, the LF variants of the invention can be administered to a patient to effect certain LF-mediated physiological changes (e.g., regulation of cytokines) without causing other physiological consequences of LF administration (e.g., neutralization of heparin by binding). The neutralized hLF and hLF variants of the invention have a variety of advantageous properties. For example, hLF variants lacking the first basic cluster are particularly useful for initiating hLF-receptor-mediated immune and inflammatory responses (e.g., reducing cytokine release, activation of natural killer cells, and anti-tumor effects), efficient receptor mediated delivery of nutritional iron, and other biological effects.

Therapeutic indications for hLF and LF variants include use in therapy or prophylaxis of infection, including local infection, large scale (bacterial) infection, blood-borne infection (sepsis) as well as inflammation resulting from an infection or non-infectious inflammatory diseases (e.g., chronic inflammatory disease of ileum or colon). Human LF and LF variants can also be used to prepare or treat organ transplant recipients or other immunosuppressed individuals (e.g., AIDS patients) against the effects of infections.

Human LF, hLF variants and neutralized hLF are also useful for reducing or inhibiting release of a cytokine, such as IL-1, IL-2 or TNFα, from lactoferrin-receptor bearing) cells in a patient, by administering lactoferrin or a lactoferrin variant. Lactoferrin has been shown to reduce the release of cytokines, e.g., IL-1, IL-2, and TNFα from cells, and inhibit proliferation in mixed lymphocyte cultures (Chierici et al., 1994, *Acta Pediatr Suppl* 402:83–89). Suppression of IL-1 and TNFα release from monocytes in response to LPS by hLF and variants is expected to down regulate recruitment and activation of neutrophils at inflammation sites (see, e.g., Lonnerdal et al., 1995, *Ann Rev Nutr* 15:93–110). The suppressive effects of LF are thought to be mediated through the binding of lactoferrin to monocyte lactoferrin-receptors (Miyazawa et al., 1991, *J. Immunol.* 146:723–729), and may be responsible for the prophylactic effect of lactoferrin in mice injected intravenously with a lethal dose of *E. coli*

(Sanchez et al., 1992, *Arch Dis Child*. 67:657–661) since LPS-mediated TNF responses in mice were attenuated by prior administration of lactoferrin (Lonnerdal et al., supra). Methods for measuring cytokine release are well known (e.g., ELISA). A reagent can be said to reduce or inhibit release of a cytokine from a cell when the level of cytokine release in the presence of the reagent is less than about 90%, more often less than about 70%, and most often less than about 50% of the levels released in the absence of the reagent under the conditions of the assay.

Human lactoferrin or a lactoferrin variants may be administered to a patient to reduce TNFα-mediated neutrophil degranulation. Neutrophils have been implicated as important mediators in both generalized and local inflammatory reactions, including sepsis, rheumatoid arthritis and ulcerative colitis. For example, clinical studies using anti-TNF monoclonal antibodies indicate that TNF, and likely the TNF-mediated activation of neutrophils, plays an important role in the pathophysiology of rheumatoid arthritis and ulcerative colitis.

Administration of human lactoferrin or a lactoferrin variants to a patient is useful for stimulating natural killer (NK) cells in the patient. Because hLF and lactoferrin variants cause stimulation of natural killer (NK) cells, the LF variants are useful for combating the targets of NK cells, e.g., tumors, viruses and intracellular pathogens. Stimulation of natural killer (NK) cells by lactoferrin has been shown in vitro (Shau et al., 1992, *J. Leukoc. Biol*. 51:343–349) and in vivo (Bezault et al., 1994, *Cancer Res*. 54:2310–2312). NK cells can be stimulated in a patient by administering to the patient a composition comprising a human lactoferrin variant and a pharmaceutical excipient. Human LF and variants may also be administered to a patient to inhibit growth of a solid tumor. A single intraperitoneal injection of LF inhibited growth of solid tumors induced by subcutaneous injection of syngeneic fibroblast-derived tumor cell lines in mice (Bezault et al., supra). LF variants will thus be useful for stimulation of NK cells without neutralization of heparin or other undesirable effects.

The invention also provides methods for inhibiting entry into a cell of viruses, for example, CMV (cytomegalovirus), HIV (human immunodeficiency viruses) or HSV1 (herpes simplex virus 1) viruses comprising administering hLF or a variant to a patient. The antiviral action is mediated by (i) interaction of hLF with cell surface proteoglycans (e.g., heparin) employed by viral particles for cell entry, and (ii) by the stimulation of NK cells by hLF and LF variants.

In another aspect, the invention provides a method for delivering iron to a lactoferrin-receptor-bearing cell in a patient by administering to the patient a composition of human lactoferrin or a lactoferrin variant which is at least about 95% saturated with iron. Administration of these compounds are beneficial, for example, in treatment of anemia or iron storage diseases. LF- or LF-variant bound iron is delivered to a cell when the polypeptide-iron complex binds to a cell receptor and is internalized by the cell. Thus the compositions disclosed herein are suitable for use in baby formula as well as for administration to patients with disturbances in iron metabolism (e.g., ferriprive anemia and iron storage diseases, and iron deficiency anemia of premature infants). LF variants may be saturated with iron following the procedure described in van Berkel et al., 1995, *Biochem J*. 312, 107–114. A lactoferrin variant composition of the present invention will typically be at least 3% saturated with iron, more usually 80% saturated, most often at least 95% saturated and often more than 99% saturated. LF variants lacking the first basic cluster, or both the first and second basic clusters are particularly useful when the iron binding activities of LF are desired and when the activities mediated by basic clusters 1 and 2 (e.g., heparin binding, high affinity receptor interaction) are not desired.

LF variants are particularly useful for the treatment of inflammatory diseases. Thus, in another aspect, the invention provides methods in which human lactoferrin or a lactoferrin variant is administered to a patient to reduce inflammation, for example in chronic inflammatory bowel disease (e.g., Crohn's disease and ulcerative colitis). Administration of hLF and hLF variants is useful for reducing reperfusion injury in a patient after myocardial infarction.

Human lactoferrin may be administered to neutralize LPS (bacterial lipopolysaccharide). The LPS binds through the first basic cluster, and is cleared from circulation via the second basic cluster.

In other aspects, the invention provides methods in which human lactoferrin or a lactoferrin variant is administered to a patient to inhibit myelopoieges and reduce production of GM-CSF.

Human LF variants lacking the second basic cluster but retaining the residues of the first basic cluster likewise have therapeutic applications. Such variants are useful, for example, to neutralize heparin or LPS without activating the LF high affinity receptor. Such variants are also used to inhibit viral entry into cells.

B. Pharmaceutical Compositions

Human lactoferrin and the lactoferrin variants of the invention may be used as pharmaceutical, food additives, nutritional supplements, and the like. The pharmaceutical compositions of the present invention are usually administered intravenously or orally. Intradermal or intramuscular administration is also possible in some circumstances.

Typically the hLF/variants will be administered along with a pharmaceutical excipient or carrier comprising any compatible, non-toxic substance suitable to deliver the polypeptides to the patient, in which case it may be referred to as a pharmaceutical composition. Sterile water, alcohol, fats, waxes, and inert solids may be used as the excipient or carrier. Pharmaceutically-acceptable adjutants, buffering agents, dispersing agents, and the like, may also be incorporated into the pharmaceutical compositions. The concentration of the polypeptide in the pharmaceutical composition can vary widely, i.e., from less than about 0.1% by weight, usually being at least about 1% by weight to as much as 20% by weight or more.

For oral administration, human lactoferrin or variant can be administered in solid dosage forms, such as capsules, tablets, and powders, or in liquid dosage forms, such as elixirs, syrups, and suspensions. The pharmaceutical compositions of the invention can be administered with a foodstuff, typically milk, e.g., bovine milk. This mode of administration will have advantages when the lactoferrin/variant is produced by expression in a transgenic animal such as a transgenic bovine, goat, or rabbit. The production of lactoferrin in transgenic bovine milk is desirable since it provides a matrix wherein little or no purification is necessary for human consumption.

A typical composition for intravenous infusion could be made up to contain 100 to 500 ml of sterile Ringer's solution and 100 to 500 mg of recombinant polypeptide. A typical pharmaceutical compositions for intramuscular injection would be made up to contain, for example, 1 ml of sterile buffered water and 1 to 100 µg of lactoferrin polypeptides. Methods for preparing parenterally administrable compositions are well known in the art and described in more detail in various sources, including, for example, *Remington's*

Pharmaceutical Science (15th ed., Mack Publishing, Easton, Pa., 1980) (incorporated by reference in its entirety for all purposes).

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective amount or dose." Such effective dosage will depend on the nature and severity of the disease or condition, and on the general state of the patient's health, but will generally range from about 1 to 500 mg of purified protein per kilogram of body weight, with dosages of from about 5 to 100 mg per kilogram being more commonly employed.

In prophylactic applications, compositions containing the compounds of the invention are administered to a patient susceptible to or otherwise at risk of a particular disease. Such an amount is defined to be a "prophylactically effective amount or dose." In this use, the precise amounts again depend on the patient's state of health and weight. Typically, the dose will range from about 1 to 500 mg of purified protein per kilogram of body weight, with dosages of from about 5 to 100 mg per kilogram being more commonly employed.

EXAMPLES

The references cited in the Examples are listed following Example 2.

Example 1

This example demonstrates that deletion of arginine residues from the first basic cluster of LF (i.e., to produce the LF variants of the invention) eliminates or reduces binding to heparin, DNA, Lipid A, and human lysozyme.

I. Materials and Methods

A. Reagents.

Mutagenic primers, S Sepharose and CNBr-activated Sepharose 4B were obtained from Pharmacia Fine chemicals AB (Uppsala, Sweden). Lipid A (from *Salmonella minnesota* Re595), heparin (sodium salt, grade I-A, from porcine intestinal mucosa), double-stranded calf thymus DNA, protamine sulfate and polyclonal rabbit anti-hLF antiserum were purchased from Sigma Chemical Co. (St. Louis, Mo., USA). Human LF was also from Sigma or purified as described below. Human lysozyme (hLZ) was purified as described [5]. NHS-LC-Biotin was from Pierce (Rockford, Ill., USA). Streptavidin biotinylated-HRPO complex and $^{125}$I were obtained from Amersham (Bucks., UK). Maxisorb and Polysorb microtiter plates were from Nunc (Roskilde, Denmark). Universal binding plates were from Costar (Cambridge, Mass., USA). All cell culture reagents were from Gibco (Paisley, UK).

B. Purification, Iron-saturation and Biotinylation of hLF.

Human LF was purified from fresh human milk by cation-exchange chromatography on S Sepharose as described (further designated as 'natural hLF') [5]. Natural hLF was 3.5% saturated with iron; complete saturation of natural hLF with iron was performed as described [5]. Natural hLF was biotinylated by incubation with a 25-fold molar excess of biotin for 2 h at 20° C. Non-bound biotin was removed by dialysis against 10 mM sodium phosphate, 0.15 M NaCl, pH 7.4 (PBS) for 16 h. Biotinylated hLF was stored at 4° C. in PBS containing 0.02% sodium azide.

C. Production and Purification of Anti-hLF Monoclonal Antibodies.

Balb/C mice were hyperimmunized by repeated intraperitoneal injections with 50 μg natural hLF as previously described [7]. Four days after the fourth injection, spleen cells were fused with SP2/0-Ag14 [ATCC CRL 1583] myeloma cells. Fusion and hybridoma selection was performed as described [8]. Culture supernatants were initially screened for the presence of specific antibodies by a radioimmunoassay (RIA), in which $^{125}$I-hLF was used as a antigen. Hybridomas producing hLF specific antibodies were cloned by repeated limiting dilution. In total, 10 different anti-hLF monoclonal antibody (mAbs) were obtained. Immunoglobulin-enriched fractions of culture supernatant were prepared by ammonium sulfate precipitation and coupled to Sepharose (20 mg of protein to 1 g of CNBr-activated Sepharose 4B) or used for the purification of anti-hLF inAb with the Repligen antibody purification kit (Cambridge, Mass., USA) as recommended by the manufacturer. The antibody concentration of purified preparations was determined by absorbance measurement at 280 nm, using an value of 1.4.

D. Expression and Purification of a N-terminal Deleted hLF Mutant.

The expression vector pCMV/hLF$^{-5N}$ encoding for amino acids Ser$^{6}$ to Lys$^{692}$ was produced with the TRANSFORMER™ site-directed mutagenesis kit as described [9]. The mutagenic primer sequence was [5' CTGTTGCTCTTGCCAGTGTTCAGTGGTGC 3'] (SEQ ID NO:7) consisting of the last 14 nucleotides of the bovine aS$_1$ casein signal sequence (underlined; [10]) fused to nucleotides 365 until 379 of the hLF cDNA (boldface; [2]) to create a deletion from nucleotide 352 until 364. After mutagenesis, the deletion was confirmed by dideoxy sequencing. Human 293(S) [ATCC CRL 1573] cells constitutively expressing pCMV/hLF$^{-5N}$ were generated as described [9] and serum-free conditioned in Dulbecco's modified Eagle medium supplemented with 50 U/ml penicillin and 50 μg/ml streptomycin. S Sepharose was batch-wise incubated with supernatant for 4 h, poured into a column and eluted with 20 mM sodium phosphate, 0.5 M NaCl, pH 7.5. The S Sepharose eluate was diluted in 20 mM sodium phosphate, pH 7.5 (buffer A), applied on a Mono S HR 5/5 cation exchange column and eluted with a linear salt gradient of 0 to 0.5 M NaCl in 60 ml of buffer A at a flow rate of 0.5 ml/min. Whereas natural hLF elutes at 0.7 M NaCl [5], the N-terminally deleted rhLF mutant (further designated as rhLF$^{-5N}$), appeared to elute at 0.33 M NaCl as determined with a hLF specific ELISA [9].

E. Isolation of N-terminally Truncated Natural hLF.

Human LF variants lacking two (Gly$^{1}$-Arg$^{2}$; designated hLF$^{-2N}$) or three (Gly$^{1}$-Arg$^{2}$-Arg$^{3}$; designated hLF$^{-3N}$) N-terminal residues were isolated from purified human milk lactoferrin of Sigma by Mono S chromatography as described above. The hLF$^{-3N}$ and hLF$^{-2N}$ species elute from Mono S at 0.5 and 0.6 M NaCl, respectively.

F. Solid-phase Ligand Binding Assays.

Microtiter plates were coated for 16 h with PBS containing 1 μg/ml lipid A (Polysorb); 10 μg/ml hLZ (Universal binding plates); 25 μg/ml heparin or dsDNA (Maxisorb, precoated with protamine sulfate (0.5 mg/ml in $H_2O$)). After washing with PBS, 0.02% (w/v) Tween-20, plates were incubated with serial dilutions of the test samples in PBS, 0.02% (w/v) Tween-20, 0.2% (w/v) gelatine (PTG). After two hours, plates were washed and incubated for 1 h with 0.4 μg/ml peroxidase-conjugated purified bovine anti-hLF in PTG containing 1% normal bovine serum. After another wash, substrate solution (0.01% (w/v) TMB, 0.003% (v/v)

$H_2O_2$ in 0.11 M sodium acetate, pH 5.5) was added. Substrate conversion was stopped by the addition of 2M $H_2SO_4$ and the absorbance at 450 mn was read with an SLT 340 ATCC rnicroplate reader (SLT-labinstruments, Austria). All incubations were performed with 100 μl volumes.

To determine the reactivity of distinct hLF species to the various ligands, serial dilutions of deleted *hLF variants and N-terminally intact natural hLF (used as a reference) were tested in parallel in the ligand binding assays and the ELISA for hLF antigen (to correct for differences in hLF concentration). The reactivity of an hLF variant towards each of the ligands was expressed as a percentage of the response with natural hLF which was arbitrarily defined as 100%.

G. Competitive Inhibition of hLF Binding to Solid-phase Ligands.

Biotinylated hLF (100 ng) was pre-incubated for 16 h with a serial dilution of competitor in PTG and added to the microtiter plates coated as described above. After 2 h, plates were washed, and incubated for 30 minutes with streptavidin biotinylated HRPO complex. After another wash, substrate solution was added. Further procedures were as described. Results were expressed as percentage inhibition of the response of biotinylated hLF without competitor.

H. Mapping of Monoclonal Anti-hLF Antibody Epitopes to the Recombinant N- or C-lobe.

Polysorb plates were coated for 16 h at 20° C. with PBS containing 1 μg/ml purified mAb. Plates were washed and incubated for 2 h with serial dilutions of natural hLF (100 ng/ml) and conditioned medium of stable 293(S) cell lines secreting either the recombinant N- or C-lobe. After washing, bound hLF was detected with peroxidase conjugated bovine anti-hLF as described.

I. RIA-procedures to Compare the Binding of Distinct hLF Species to Anti-hLF-Sepharoses.

Technical procedures of these RIAs were as described for the RIA for hLF antigen. Briefly, anti-hLF mAbs coupled to Sepharose were incubated with serial dilutions of hLF variants. Bound hLF was detected by subsequent incubation with polyclonal $^{125}$I-anti-hLF antibodies. Results were expressed as percentage binding of the total amount of labeled antibodies added.

II. Results

A. Human Lactoferrin Specifically Interacts with Heparin, Lipid, hLZ and DNA.

Figure 1:
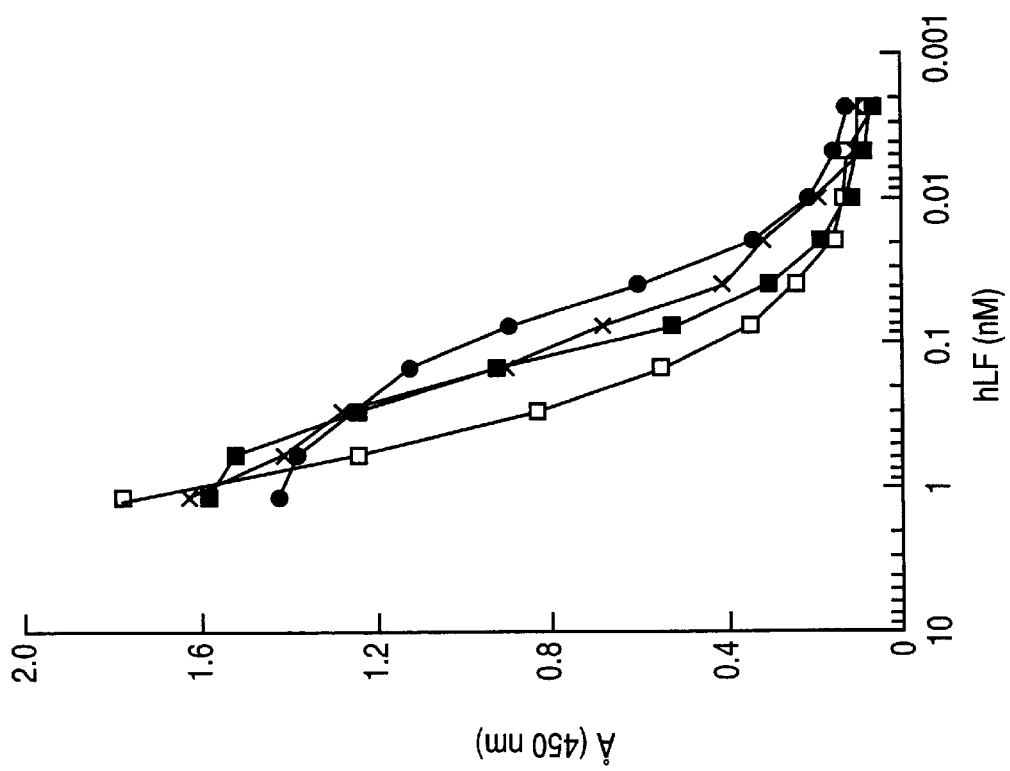
FIG. 1 shows binding of hLF to solid-phase heparin, lipid A, hLZ and DNA. Serial dilutions of purified natural hLF (50 ng/ml) were incubated with heparin (●), lipid A (X), hLZ (□) or dsDNA (■) coated to microtiter plates as described. Bound hLF was detected by subsequent incubation with peroxidase-labelled bovine anti-hLF. The $A_{450}$ values measured after substrate conversion was stopped with sulfuric acid are indicated on the ordinate. The hLF concentration in the well is indicated on the abscissa.

Solid-phase ligand binding assays were developed to study the interaction of hLF with heparin, lipid A, hLZ and DNA. FIG. 1 shows the binding of natural hLF to each of the ligands immobilized onto mnicrotiter plates. No binding was observed when hLF was incubated with uncoated plates or plates coated with bovine serum albumin (results not shown). These results indicate that hLF specifically binds to heparin, lipid A, hLZ and DNA.

Next, the binding of natural and iron-saturated hLF to these ligands was characterized. Table 1 shows that both hLF species with identical $IC_{50}$ values, competed for the binding of hLF to heparin, lipid A and hLZ indicating identical affinities of natural and iron-saturated hLF for each ligand. No inhibition was found with human transferring (hTF), a metal binding protein closely related to hLF in size and structure, confirming the specificity of hLF-ligand interaction.

The binding of hLF to heparin and DNA involves electrostatic interaction, which can be disrupted by increasing the ionic strength. FIG. 2 shows the effect of the NaCl concentration on the binding of hLF to LPS and hLZ. At physiological NaCl concentration (0.15 M) about 40% of hLF bound to LPS and hLZ. Decreasing the salt concentration increased hLF binding to LPS and hLZ up to about 75% and 55% at 0.013 M NaCl, respectively, whereas increasing NaCl over 0.4 M NaCl abolished the binding. These results illustrate the ionic strength dependence of hLF binding to ligands and suggest that the highly cationic N-terminus of the protein is involved in the electrostatic interaction of hLF with the ligands.

TABLE 1

Inhibition of hLF-ligand interaction with unlabelled hLF but not with hTF.

| | $IC_{50}{}^a$ Competitor (nM) | | |
|---|---|---|---|
| Ligand | Natural hLF | Iron-saturated hLF | hTF |
| Heparin | 9.5 ± 1.9 | 10.4 ± 1.5 | no competition |
| Lipid | 1.7 ± 0.5 | 1.3 ± 0.4 | no competition |
| hLZ | 11.2 ± 2.2 | 15.4 ± 4.0 | no competition |

$^a$The concentration of competitor to obtain 50% inhibition of the response with 12.5 nM biotinylated hLF. The results are the mean ± SD of at least 4 independent experiments.

B. The Region $Arg^2$-$Arg^3$-$Arg^4$-$Arg^5$ is Essential in Binding of hLF to Heparin, Lipid A, hLZ and DNA.

To delineate the contribution of the four consecutive arginines ('first basic cluster') in the hLF N-terminus in hLF-ligand interaction, the binding of N-terminally deleted hLF species to heparin, lipid A, hLZ and DNA was studied. Natural hLF lacking $Gly^1$-$Arg^2$, designated $hLF^{-2N}$, showed a 2, 1.5, 3 and 3-fold lower affinity for heparin, lipid A, hLZ and DNA, respectively, than N-terminally intact hLF (Table 2). Natural hLF lacking $Gly^1$-$Arg^2$-$Arg^3$, designated $hLF^{-3N}$, showed a 8, 4, 17 and 17 fold lower affinity for heparin, lipid A, hLZ and DNA, respectively. The binding of hLF was absent with the mutant $rhLF^{-5N}$, which lacks $Arg^2$-$Arg^3$-$Arg^4$-$Arg^5$ (SEQ ID NO:1) (Table 2). These results indicate that all four arginines contribute to the interaction of hLF with heparin, lipid A, hLZ and DNA and that the removal of the first basic cluster abrogates the interaction of hLF with these ligands.

TABLE 2

Binding of N-terminally deleted hLF species to heparin, lipid A, hLZ and DNA

| | Reactivity (%) | | | |
|---|---|---|---|---|
| | Heparin | Lipid A | hLZ | DNA |
| Native hLF | 100 | 100 | 100 | 100 |
| $hLF^{-2N}$ | 55.6 ± 4.1 | 67.8 ± 10.2 | 37.5 ± 12.4 | 31.2 ± 2.1 |
| $hLF^{-3N}$ | 12.7 ± 2.0 | 25.7 ± 3.1 | 5.1 ± 2.1 | 5.8 ± 1.2 |
| $rhLF^{-5N}$ | no binding | no binding | no binding | no binding |

C. Monoclonal Antibody E11 Inhibits hLF-ligand Interaction.

Figure 3:
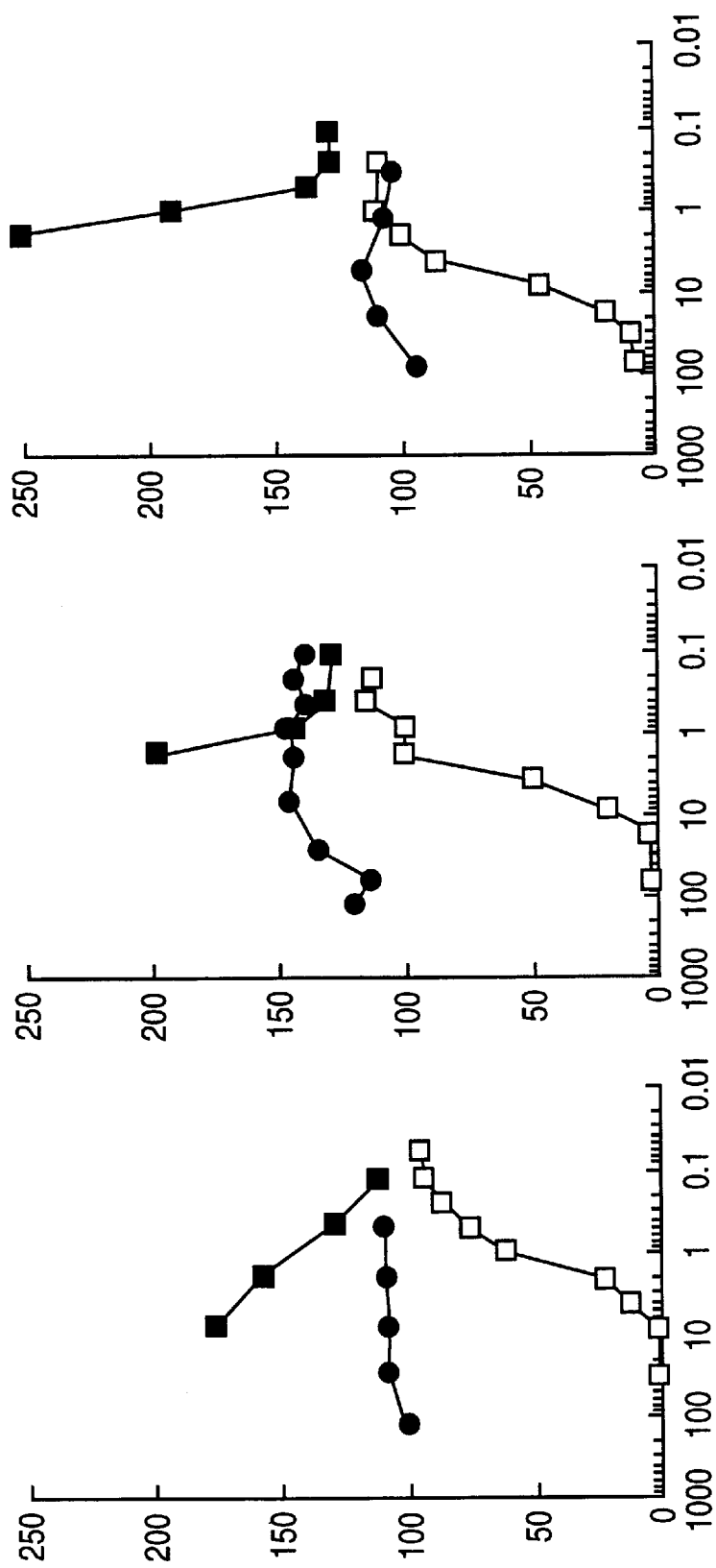
FIG. 3 shows competitive inhibition by anti-hLF mAb E11 of hLF binding to heparin, lipid A and hLZ. Plates were coated with heparin (left), lipid A (middle) and hLZ (right). Biotinylated hLF was preincubated with serial dilutions of anti-hLF mAb E11 (□), anti-hLF mAb E3 (■) and a control mAb (●) as described. The residual hLF binding in the presence of competitor (by reference to hLF without competitor; 100%) is indicated on the ordinate. The mAb concentration in the well (nM) is indicated on the abscissa.

Ten different purified anti-hLF mAbs were tested for their ability to inhibit the binding of hLF to immobilized ligands. The results in FIG. 3 show that preincubation of 5hLF with anti-hLF mAb E11 could completely block the interaction of hLF with heparin (A), lipid A (B) and hLZ (C), whereas a control mAb did not affect hLF binding. The differences in molar ratio of mAb E11 and hLF in the preincubation mixture, required to completely prevent hLF binding to the solid phase ligands most likely results from differences in the affinities of hLF for each ligand and mAb E11 (due to slight differences in the interface of hLF with the different ligands and the mAb) as well as differences in the amount of immobilized ligands. Surprisingly, all anti-hLF mAbs, other than E11 increased hLF-ligand interaction (FIG. 3 shows representative results with mAb E3). The latter probably is due to the cross-linking of two solid-phase bound biotinylated hLF molecules by the mAbs with the dimeric complex having a higher affinity for immobilized ligands than monomeric hLF.

D. The Epitope of mAb E11 Resides in the N-terminus of hLF.

In order to localize the mAb E11 epitope on hLF, serial dilutions of natural hLF and culture supernatant containing either the recombinant N- or C-lobe was added to E11 immobilized onto microtiter plates. FIG. 4A shows that E11 binds to the recombinant N-lobe. FIGS. 4B and C show control experiments in which anti N-(E3; FIG. 4B) and anti C-lobe (E19; FIG. 4C) mAb were used. The comparative analysis of N-lobe antigen detection in the rN-lobe with that in natural hLF in the ELISAs with mAb E11 (FIG. 4A) and mAb E3 (FIG. 4B), suggest that the polyclonal anti-hLF used for the detection of bound hLF contains more antibodies directed to the mAb E3 epitope than those against E11 epitope.

The two N-lobe specific mAbs E3 and E11 (FIGS. 4A–4C) were coupled to Sepharose and incubated with serial dilutions of purified samples of $rhLF^{-5N}$, $hLF^{-3N}$, $hLF^{-2N}$ and natural hLF. Dose response curves of these hLF species in the RIA with E3-Sepharose showed identical slopes and maximal responses (FIG. 5B), suggesting that N-terminally deleted hLF and natural hLF is equally well bound by mAb E3 and detected by the polyclonal antibody. Comparison of the responses in the RIAs with E3 and E11 indicates that the removal of N-terminal residues in $rhLF^{-5N}$ and $hLF^{-3N}$ affects the binding of these hLF variants by E11 (as manifested by decreased plateau values and non-parallel curves). These results imply that N-terminal arginine residues are part of the E11 epitope. The observation that the binding of $rhLF^{-5N}$ to mnAb E11 was not completely abrogated, indicates that the E11 epitope also contains residues C-terminal of $Arg^5$.

III Discussion

These data show that a single region, $Arg^2$-$Arg^3$-$Arg^4$-$Arg^5$ (SEQ ID NO:1), determines the specific electrostatic interaction of hLF with hLZ and polyanions like heparin, lipid A, DNA. The data unequivocally demonstrate the essential role of the N-terminal penultimate stretch of four arginines in the interaction of hLF with heparin, lipid A, hLZ and DNA. Binding was reduced on removal of consecutive Arg residues and was abolished with $rhLF^{-5N}$, a mutant which lacks $Arg^2$ to $Arg^5$. The latter observation is in line with Mann et al., supra, who concluded that $Arg^4$ and $Arg^5$ are crucial for the hLF-GAG interaction. However, the results shown here with natural hLF species lacking one or two N-terminal arginine residues clearly demonstrate that $Arg^2$ and $Arg^3$ also contribute to the interaction of hLF with heparin, lipid A, hLZ and DNA. It is noteworthy that residues $Arg^4$ and $Arg^5$ are conserved in human, ovine, equine, bovine and porcine LF. Murine LF (mLF) lacks a pair of basic residues at these positions [32]. Indeed, mnLF elutes at 0.3 M NaCl on Mono S chromatography [1], i.e. virtually at the same position as $rhLF^{-5N}$ and does not compete for the binding of hLF to ligands.

Figure 5B:
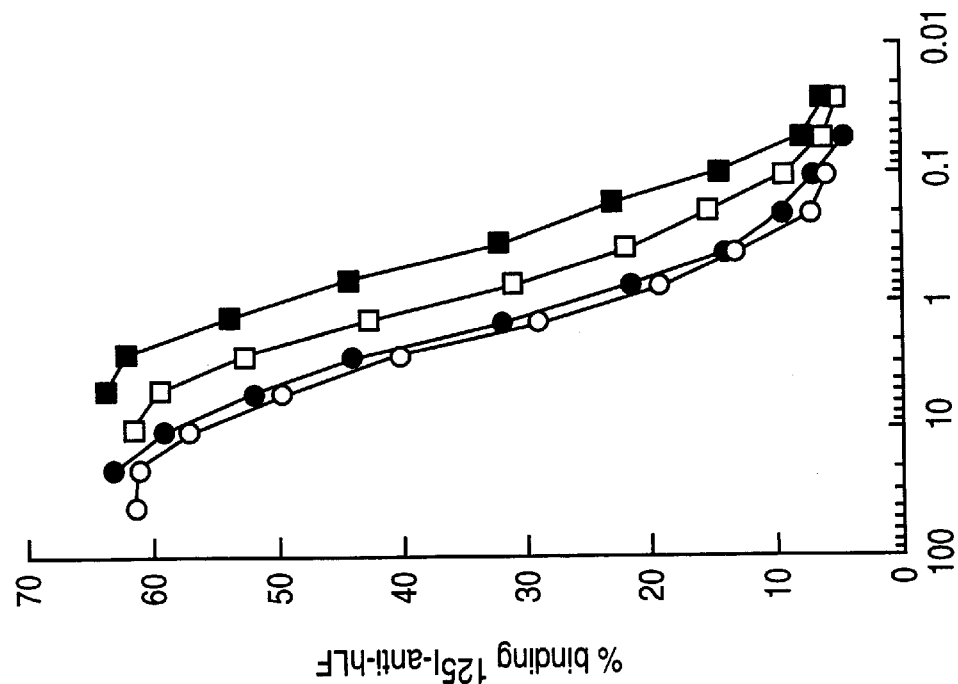
FIGS. 5A and 5B show the comparison of the binding of N-temninally deleted and natural hLF to anti-hLF mAb E11 and E3. Serial dilutions of natural hLF (40 μg/ml, ■), $hLF^{-2N}$ (20 μg/ml, □), $hLF^{-3N}$ (10 μg/ml, ●) and $rhLF^{-5N}$ (7 μg/ml, ○) were incubated with mAb E11 (FIG. 5A) or E3 (FIG. 5B) coupled to Sepharose. Bound hLF was detected by subsequent incubation with polyclonal $^{125}$I-anti-hLF antibodies. Results were expressed as percentage binding of the total amount of antibodies added.
Figure 5A:
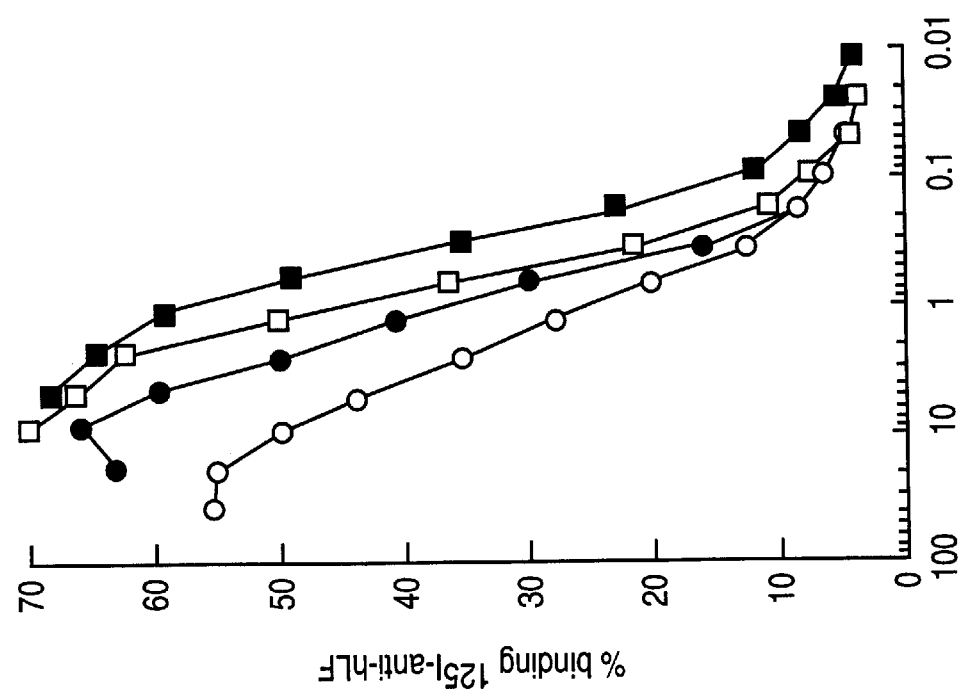

The Mutant $rhLF^{-5N}$ had lost its ability to interact with any of the ligands even when concentrations up to 20 μg/ml were added in the solid-phase binding assay. Moreover no binding of the recombinant C-lobe to LPS and heparin is detectable. Apparently, the basic cluster $Arg^{342}$-$Arg^{343}$-$Ala^{344}$-$Arg^{345}$ (SEQ ID NO:8) in the C-lobe, which is homologous to the first basic cluster $Arg^2$-$Arg^3$-$Arg^4$-$Arg^5$ (SEQ ID NO:1) in the N-lobe, is not able to interact with these ligands. This may be due to the three consecutive glutamine acids ($Glu^{336}$-$Glu^{337}$-$Glu^{338}$) preceding $Arg^{342}$-$Arg^{343}$-$Arg^{344}$-$Arg^{345}$ (SEQ ID NO:8) and/or the surface exposure of positive charge. Minor contamination of the C-terminal tryptic fragment with Neyninal tryptic fragments likely explains the apparent binding of the C-terminal tryptic fragment to LPS [11]. Iron-free and iron-saturated hLF have been found to possess the same capacity to neutralize heparin coagulant activities [3]. It is shown in Table 1 that natural and iron-saturated hLF compete equally well competed for the binding of hLF to heparin, lipid A and hLZ, suggesting that both hLF species have identical affinities for these ligands. Thus, the conformational change which occurs in hLF upon the incorporation of iron apparently does not affect the projection of the N-terminal ligand binding site. Indeed, crystallography has shown that on saturation of hLF with iron, the two domains of the N-lobe rotate as rigid bodies, leaving the relative position of the N-terminus essentially unaffected [12]. Monoclonal E11 specifically inhibited the interaction of hLF with lipid A, heparin and hLZ and was mapped to bind to or in the vicinity of $Arg^2$-$Arg^3$-$Arg^4$-$Arg^5$ (SEQ ID NO:1) (FIG. 5A and 5B). This confirms the importance of this region in hLF-ligand interaction.

We have previously found that many commercially available preparations of human milk LF, contain variable amounts of hLF species lacking 3 or 2 N-terminal residues eluting at 0.5 and 0.6 M NaCl, whereas N-terminally intact hLF elutes from Mono S at 0.7 M NaCl. Although hLF is very resistant to in vitro tryptic proteolysis as assessed by SDS-PAGE analysis, experiments have demonstrated cleavage occurs first and relatively readily at N-terminal arginines 2 and 3. Preparations containing much hLF cleaved at its N-terminus will likely display a lower specific activity than intact hLF in those biological assays in which interaction with heparin, LPS, hLZ and DNA is the basis to hLF action. The capacity of cleaved hLF to neutralize the heparin anticoagulant activity and thus enhance thrombin formation and coagulation will probably be lower than that of intact hLF. Cleaved hLF may less effectively prevent infection with CMV if the interference by hLF of virus binding to cell surface GAGs indeed is the basis for its antiviral effect. The ability of cleaved hLF to inhibit LPS induced priming of neutrophils is likely to be reduced. Similarly, effects on gene transcription through binding to nuclear DNA is less likely to occur with cleaved hLF. The antibacterial activity of cleaved hLF towards some Gram-negative bacteria will be reduced if the binding of hLF to LPS and effects therefrom [6] is an important determinant in the overall antibacterial effect. The presence of a ligand in biological systems, either on purpose or as a contamination may also affect the biological activity of hLF if the interaction with another ligand is key to activity or when the activity of the complex overrides effects of hLF alone. For example, heparin has been shown to block the binding of hLF to Staphylococcus aureus [13]. RNA and DNA inhibited the ability of hLF to increase natural killer cell cytotoxicity [14]. Preincubation of bLF with lipid A could completely block the binding to heparin. Contamination of hLF with LPS removes the myelosuppressive effect of hLF [33], the suppression of monocytic IL-1 and TNF release and the inhibition of LPS priming of neutrophils for enhanced fMLP-triggered superoxide release [4]. Batch-wiser extraction of hLF from milk at 0.4 M NaCl is an effective means of preventing contamination of this protein with hLZ and LPS. It is however also likely that N-terminally truncated hLF may display a higher specific activity or otherwise different performance than intact hLF in some other biological systems. The rapid hepatic clearance of hLF from the circulation involves at least two classes of hLF binding sites, i.e. a large number of low affinity binding sites (presumably cell-associated proteoglycans) and a lower number of high affinity binding sites representing the chylomicron remnant receptor and/or the LDL-receptor-related protein (LRP) [15, 16]. Ziere et al showed that the binding to rat hepatocyte chylomicron remnant receptor and subsequent internalization was increased with hLF from which the first 14 N-terminal residues had been removed by aminopeptidase treatment [16]. With N-terminally truncated hLF species, 'low-affinity' binding of cleaved hLF to cell surface associated sulfated molecules, representing the abundant low affinity binding sites on Jurkat human lymphoblastic T-cells. These results provide clear evidence that the binding of hLF to the specific receptor involves the second basic cluster of hLF. Limited N-terminal proteolysis of hLF may thus shift a greater proportion of hLF to bind to the specific receptor and thus presumably alter hLF immunomodulatory activity.

Example 2

This example demonstrates that the LF variants bind with high affinity to the Jurkat cell LF receptor but does not bind, or binds with low affinity relative to natural LF, to sulfated cell surface molecules.

I. Materials and Methods

A. Chemicals

Soybean Ms psin inhibitor (SBTI, type I-S), bovine pancreatic typsin (type III-S) and sodium chlorate were purchased from Sigma Chemical Co. (St. Louis, Mo., U.S.A.). Restriction endonucleases and oligonucleotides were obtained from Eurogentec (Seraing, Belgium). T4 ligase, calf alkaline phosphatase and pBluescript SK were from Stratagene (La Jolla, U.S.A.). Sequanase DNA sequencing kit was obtained from United States Biochemical Corporation (Cleveland, U.S.A.). Baculogold kit containing linearized AcNPV DNA and agarose were purchased from Phaigen (San Diego, U.S.A.). Plasmid pVL1392 and cell line *Spodoptera frugiperda* (Sf9) were kindly provided by Dr. C. Auriault (Institut Pasteur, Lille, France). Carrier-free $Na^{125}I$ was from ICN Pharmaceuticals (Orsay, France) and Iodo-Beads were from Pierce (Rockford, U.S.A.). Sephadex G25 PD-10 columns were purchased from Pharmacia-LKB Biotechnology (Uppsala, Sweden). RPMI 1640 medium and fetal calf serum (FCS) were from Techgen International (Les Ulis, France) and D. Dutscher (Brumath, France), respectively. SF900II insect cell medium and gentamycin were from Gibco BRL (Cergy-Pontoise, France). All other chemicals were of analytical grade.

B. Proteins

Native hLf was purified from fresh human milk of a single donor by ion-exchange chromatography as previously described [24]. Bovine Lf was provided by Biopole (Brussels, Belgium). Murine Lf was isolated from mouse milk as follows: mouse milk was diluted two-fold in phosphate buffered saline, pH 7.5 (PBS) containing 0.01% (w/v) SBTI, 10 mM benzamidine hydrochloride, 0.05% hexadimethrine bromide (Polybrene), 10 mM EDTA, 1 mM PMSF and 0.8 M NaCl. Diluted milk was rotated in a swing-out rotor at 40,000 g for 1 h at 4° C. to separate the whey, caseins (pellet) and fat. The whey fraction was diluted in 20 mM sodium phosphate, pH 7.5 (buffer A), and applied to a S-Sepharose column. The column was washed with buffer A containing 0.2 M NaCl, and eluted by blocking with buffer A containing 0.5 M NaCl. S-Sepharose eluted fractions were rerun on a Mono S HR 5/5 column (Pharmacia, Upsalla, Sweden) in buffer A. Bound proteins were eluted with a linear salt gradient of 0–0.5 M NaCl in 15 ml buffer A at a flow rate of 0.5 ml/min. Murine Lf eluting at 0.28 M NaCl was used for further experiments. Homogeneity of the proteins was checked by SDS/PAGE [25]. Iron saturation of lactoferrins was carried out as described elsewhere [26]. Human serum transferring was from Sigma (St. Louis, Mo., U.S.A.). Non-modified rhLf was obtained as described in [27].

C. Expression and Purification of a N-terminally Deleted hLf Mutant Lacking Amino Acids 1–5

A fall-length 2.3 kbp cDNA coding for hLf was obtained from a human mammary-gland cDNA library (Clontech, Palo Alto, Calif., U.S.A.), as described [28]. The Sculptor in vitro mutagenesis system kit (Amersham International, Amersham, Bucks, U.K.) was used to delete the sequence 5'-GGCCGTAGGAGAAGG-3' (SEQ ID NO:9) coding for $Gly^1$-$Arg^2$-$Arg^3$-$Arg^4$-$Arg^5$ (SEQ IDNO:10) of hLf [19]. For that purpose, a mutagenic oligonucleotide: 5'-CTGTGTCTGGCTAGTGTTCAGTGGTG-3' (SEQ ID NO:11) was synthesized. The template for mutagenesis was the phage M13mp11, which contains a 310 bp EcoRI-AccI fragment of the coding sequence (nucleotides 295–606 [19]) cloned into pBluescript SK plasmid [28]. After mutagenesis, the deletion was confirmed by DNA sequence analysis and the mutated EcoRI-AccI fragment was ligated back into pBluescript SK with the 3' complementary part of the full length cDNA of hLf as described [28]. Finally, the mutated cDNA was subdloned into pVL1392 yielding the pVL1392-$rhLf^{-5N}$ construct. Production of recombinant baculovirus, Sf9 insect cell culture and production of the N-terminally deleted rhLf mutant (hereafter designated '$rhLf^{-5N}$') were performed as reported in [27]. The recombinant protein was purified from the cell culture medium on a SP-Sepharose Fast Flow column equilibrated with 0.2 M sodium acetate, pH 7.8 and eluted with a linear salt gradient from 0 to 1 M NaCl. The purity of $rhLf^{-5N}$ was checked on a 7.5% SDS-PAGE. The N-terminal amino acid sequence analysis of $rhLf^{-5N}$ was performed by the Edman degradation procedure, using an Applied BioSystem 477 Protein Sequencer.

D. SDS-PAGE Analysis

SDS-PAGE of non-reduced and reduced hLf was performed as described [18]. Proteins were stained with Coomassie Brilliant Blue and hLf protein bands were quantitated by densitometry using IPlabOel software of Signal Analytics (Vienna, Va., U.S.A.).

E. Radiolabeling of Proteins $^{125}I$ labeling of different lactoferrin variants was carried out using Iodo-beads as a catalyst. Two lodo-beads were washed twice with 1 ml PBS in a 1.5 ml polypropylene centrifuge tube and preincubated at room temperature with 0.2 mCi of radioactive iodine in 100 ml PBS. 100 mg protein in 100 ml PBS were then added to the mixture and incubated for 10 min at 4° C. The volume was adjusted to 500 ml with PBS and free iodine was removed by gel filtration on a PD-10 column equilibrated in serum-free RPMI 1640. Specific activity of the radioiodinated protein was estimated by measuring the absorbance at 280 nm and counting on a Compugamma LKB-Wallac (Turku, Finland) γ-radiation counter.

F. Cell Culture

Jurkat cells were routinely grown at 37° C. in a humidified atmosphere under 5% $CO_2$ in RPMI 1640 medium pH 7.4, containing 5 mg/ml gentamycin, 2 mM L-glutamine, 20 mM Hepes and 10% heat-inactivated FCS. Cells were kept in the logarithmic growth phase and diluted to a cell density of 4×10$^5$/ml (determined by using a cell counter) one day before the binding experiments. After 24 h, cell viability was checked using the Trypan Blue stain. Cells were then washed twice in ice-cold serum-free RPMI 1640 and harvested by centrifugation at 4° C., 200 g for 10 min.

G. Treatment of Jurkat Cells with Sodium Chlorate

Jurkat cells were diluted to a cell density of 4×10$^5$/ml in fresh RPMI 1640 medium containing 10% FCS, 5 mg/ml gentamycin and 30 mM sodium chlorate. Cells incubated in the absence of sodium chlorate were used as a control. After 24 h chlorate treatment, cells were counted and cell viability was assessed with Trypan Blue.

H. Cell Binding Experiments

Equilibrium binding experiments were performed in serum-free RPMI 1640 containing 0.4% (w/v) human serum transferring to prevent non-specific binding of hLf to cells or to plastic. Aliquots (100 ml) containing 5.10$^5$ cells were added to 1.5 ml polypropylene centrifuge tubes and incubated with serial dilutions of $^{125}$I-labeled protein (concentrations ranging from 0 to 80 nM). Incubation of cells with proteins was performed at 4° C. for 1 h in the presence of 0.01% (w/v) sodium azide to prevent ligand internalization. Cells were washed three times by centrifugation at 180 g for 7 min with 1 ml RPMI, resuspended in 0.5 ml PBS and bound radioactivity was measured. Non-specific binding measured in the presence of a 100-fold molar excess of unlabeled hLf was typically around 25% of the total binding and was subtracted from total binding to obtain the specific binding. Binding parameters (Kd and number of binding sites per cell) were calculated by Scatchard-plot analysis [29] using the Enzfitter program software 1.05 (BioSoft).

II. Results

A. Preparation of N-terminally Deleted hLf Variants

Limited proteolysis of hLf by trypsin, a serine protease which cleaves specifically after Arg and Lys residues was studied. Five mg amounts of native hLf were incubated with trypsin at an enzyme: substrate molar ratio of 1:8 at 37° C. in PBS. Digestion was stopped after 1, 5, 25 min and 3 h by the addition of a 12-fold molar excess of SBTI and N-terminal integrity was assessed by analytical Mono S chromatography [18]. Bound protein was eluted with a linear salt gradient of 0–1.0 M NaCl in 30 ml buffer A at a flow rate of 1.0 ml/min. Eluted protein was detected by absorbance measurement at 280 nm. Relative amounts (%) were calculated by integrating peak areas. Table 3 shows that after 1 min of trypsinization, all hLf molecules had been N-terminally cleaved, since 20% and 80% of hLf molecules lacked residues Gly$^1$-Arg$^2$-Arg$^3$ or Gly$^1$-Arg$^2$, respectively. After 3 h, 2%, 49% and 42% of total hLf molecules lacked residues Gly$^1$-Arg$^2$-Arg$^3$-Arg$^4$ (SEQ ID NO:14) (further designated as 'hLf$^{-4N}$'), Gly$^1$-Arg$^2$-Arg$^3$ (further designated as 'hLf$^{-3N}$') and Gly$^1$-Arg$^2$ (further designated as 'hLf$^{-2N}$'), respectively.

TABLE 3

Relative amounts of N-terminal deleted hLf variants obtained after limited tryptic proteolysis of native hLf

| Time (min) | Relative amount (%) of total hLF | | | |
|---|---|---|---|---|
| | hLF$^{-4N}$ | hLF$^{-3N}$ | hLF$^{-2N}$ | intact hLF |
| 0 | 0 | 0 | 0 | 100 |
| 1 | 0 | 20 | 80 | 0 |
| 5 | 0 | 22 | 78 | 0 |
| 25 | 1.0 | 28 | 70 | 0 |
| 180 | 2.0 | 49 | 42 | 0 |

Figure 6:
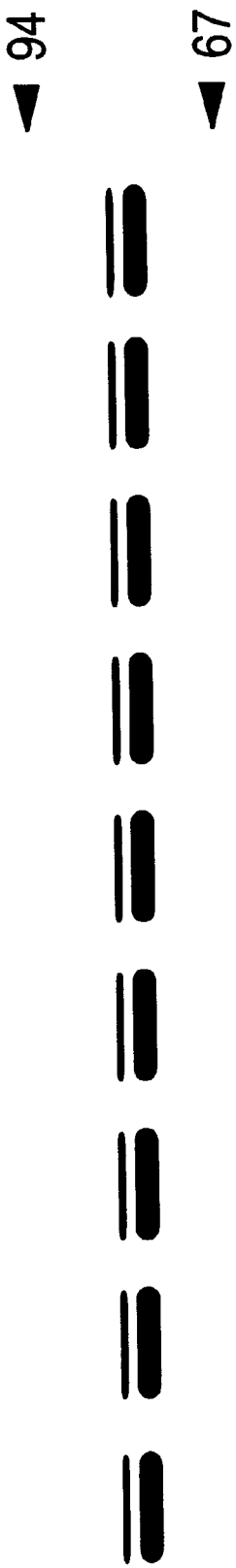
FIG. 6 shows non-reduced SDS-PAGE analysis of purified N-terminally deleted hLf obtained after Mono S Chromatography of limitedly proteolyzed hLf Fractions containing limitedly proteolyzed hLf that were eluted from Mono S at 0.5 and 0.6 NaCl were diluted in non-reducing sample buffer and applied to SDS-PAGE (12.5% w/v) after boiling for 5 min [van Berkel et al., 1995, Biochem. J., 312, 107–114]. A sample of native hLf (lane 1) and samples of $hLF^{-2N}$ and $hLF^{-3N}$ isolated from a 1 minute digest (lanes 2 and 3), from a 5 minute digest (lanes 4 and 5), from a 25 min digest (lanes 6 and 7) and from a 180 min digest (lanes 8 and 9). All lanes contain 5 μg of protein. Numbers on the right ($10^{-3}$×Mr) indicate the migration of the protein standards. Similar results were obtained with reduced SDS-PAGE analysis of the samples (data not shown).

Human Lf is cleaved by trypsin after Lys$^{283}$, which results in the major N- and C-terminal tryptic fragments of MT 39,000 and 51,000 [30, 31]. SDS-PAGE analysis of non-reduced samples of hLf$^{-2N}$ and hLf$^{-3N}$ obtained after trypsinization for 1, 5, 25 min and 3 h revealed that tryptic proteolysis of the peptidic linkages after Arg$^2$ and Arg$^3$ occurs before cleavage after Lys$^{283}$, i.e. no tryptic cleavage fragments of Mr 39,000 and Mr 51,000 were observed in samples obtained from the 1 and 5 min digest (FIG. 6). After 25 min, the presence of minor amounts of N- and C-terminal tryptic fragments was observed. Less than 1% of total protein had been cleaved into fragments of Mr 39,000 and 51,000. After 3 h, these fragments represented about 5% of total hLf.

B. Preparation of the Recombinant hLf Lacking Residues 1–5

Arg$^5$ could not be cleaved by limited trypsin treatment of native hLf. Therefore, a recombinant hLf (rhLf) mutant lacking the first five N-terminal amino acids further designated as rhLf$^{-5N}$ was expressed. Linearized baculovirus and pVL1392-rhLf$^{-5N}$ were used to transform Sf9 cells and a rhLf$^{-5N}$-expressing clone was selected by ELISA [17]. Culture medium of this clone was loaded on a SP-Sepharose Fast Flow column and rhLf$^{-5N}$ was eluted as a single peak at 0.4 M NaCl. The protein appeared as a single protein band of Mr 78,000 by SDS-PAGE. The N-terminus of rhLf$^{-5N}$, Ser-Val-Gln-Trp-Cys-Ala-Val (SEQ ID NO:12), was confirmed by amino acid sequence analysis. Recombinant hLf$^-$$_{5N}$ was obtained with a maximal yield of 8 mg/ml of culture medium.

C. Binding of Native Lf and N-terminally Deleted hLF Species to Jurkat Cells

Figure 7:
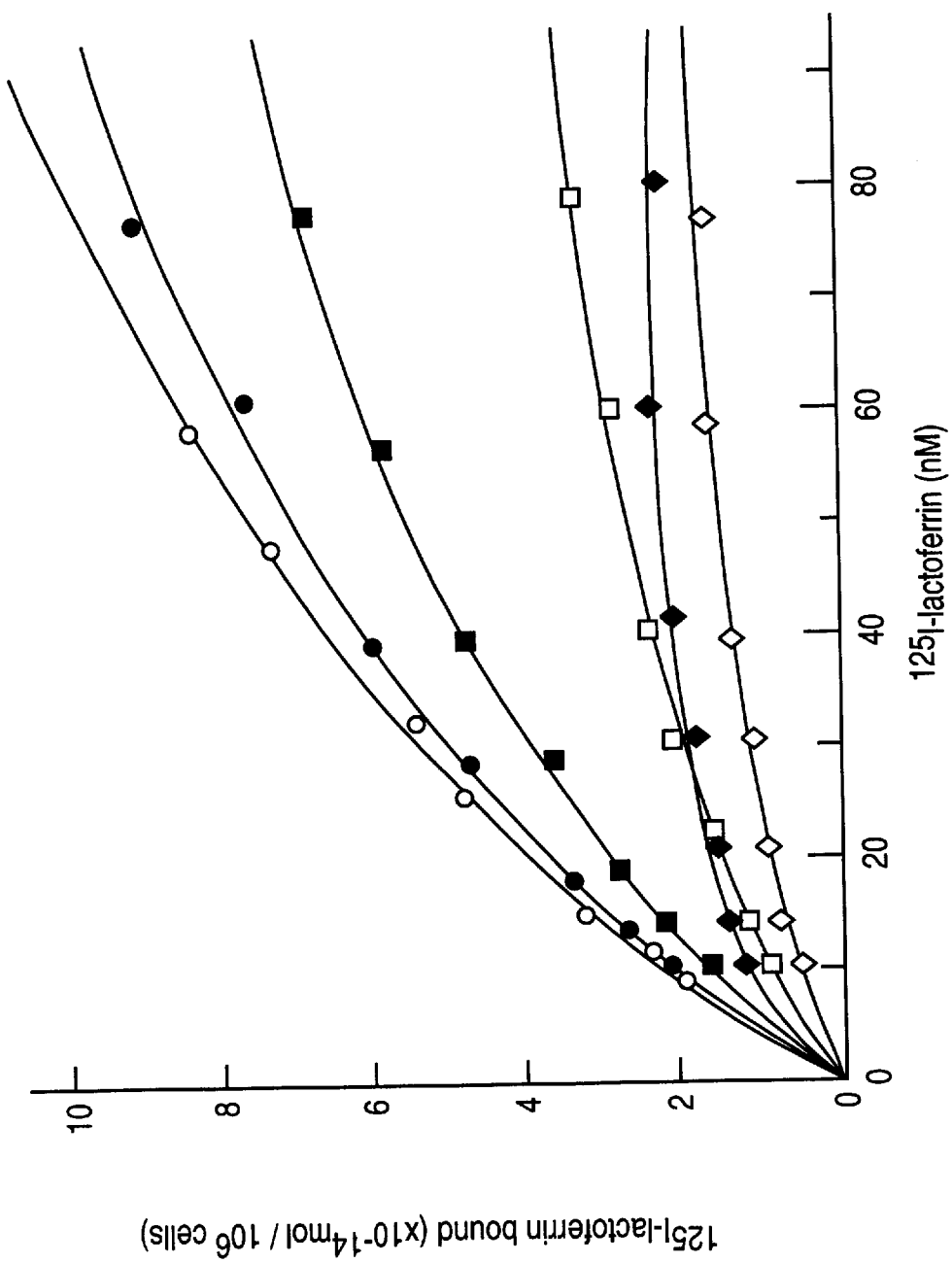
FIG. 7 shows binding of N-terminally deleted hLf variants to Jurkat cells as a function of concentration. Curves correspond to the specific binding of hLf (●); rhLf (○); $hLF^{-2N}$ (■); $hLF^{-3N}$ (□); $hLF^{-4N}$ (◇) and $rhLF^{-5N}$ (♦). Values are means of two to three separate experiments in duplicate.
Figure 8A:
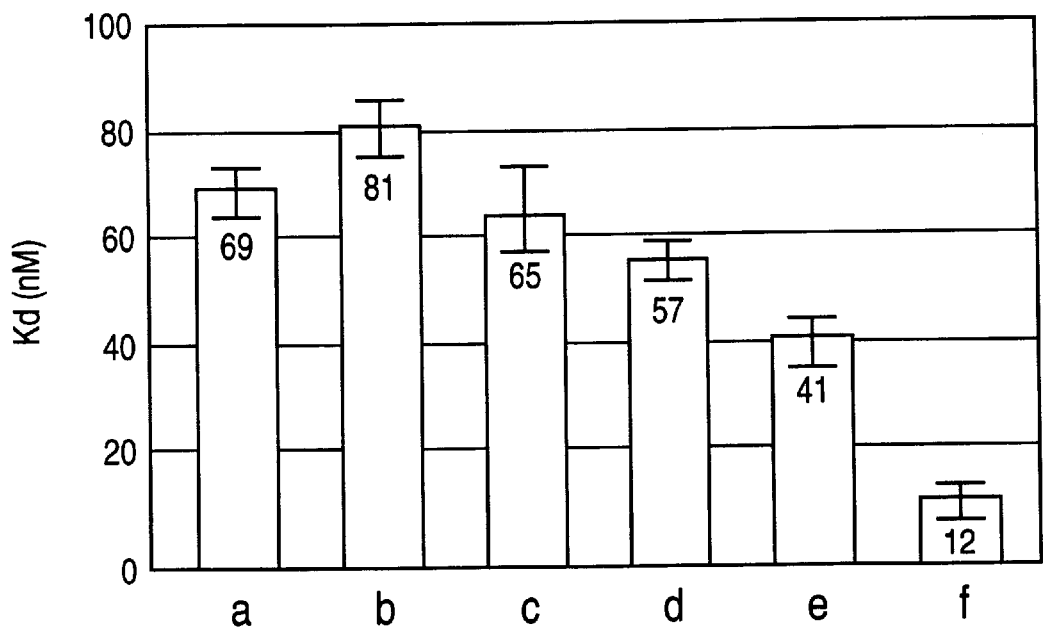
FIGS. 8A and 8B show binding parameters of N-terminally deleted hLf variants to Jurkat cells. Dissociation constants (FIG. 8A) and numbers of binding sites per cell (FIG. 8B) of hLf(1); rhLf(2); $hLF^{-2N}$ (3); $hLF^{-3N}$ (4); $hLF^{-4N}$ (5) and $rHLF^{-5N}$ (6). Values are means (±S.E.M.) of two to three separate experiments in duplicate.

To delineate the role of Arg$^2$-Arg$^3$-Arg$^4$-Arg$^5$ (SEQ ID NO:1) ('first basic cluster') of hLf in the binding to Jurkat human lymphoblastic T-cells, the binding of $^{125}$I-labeled native hLf and N-terminally deleted hLf species at concentrations ranging from 0 to 80 nM was studied. FIG. 7 shows that the binding of all hLf species was concentration-dependent and saturable. Moreover, binding of all proteins was inhibited for about 75% in the presence of a 100-fold molar excess of unlabeled lactoferrin, suggesting that the binding was reversible and specific. Scatchard analysis revealed that, in the range of hLf concentrations used, the affinity of N-terminally deleted hLf was significantly increased when compared to N-terminal intact hLf (FIG. 8A). The Kd shifted from 69 or 81 nM for hLf or rhLf to 65, 57 and 41 nM for hLf$^{-2N}$, hLf$^{-3N}$ and hLf$^{-4N}$, respectively. A markedly decreased Kd of 12.4 nM was observed for rhLf$^{-5N}$. In addition, it was found that the number of binding sites per cell decreased from 110,000 for N-terminal intact hLf to 20,000 for both hLf$^{-4N}$ and rhLf$^{-5N}$ (FIG. 8B). hLf$^{-2N}$ and hLf$^{-3N}$ bound to about 75,000 and 35,000 binding sites, respectively. These results suggest that the binding of hLf to approximately 80,000 binding sites on Jurkat cells depends on the presence of Gly$^1$-Arg$^2$-Arg$^3$-Arg$^4$ (SEQ ID NO:14).

Figure 8B:
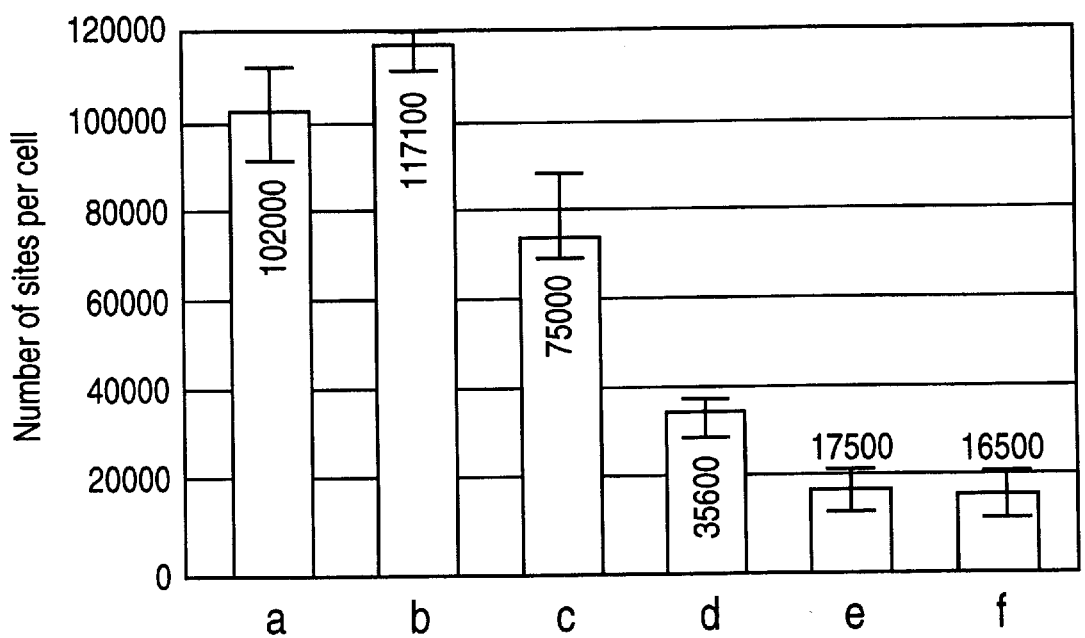
Figure 9:
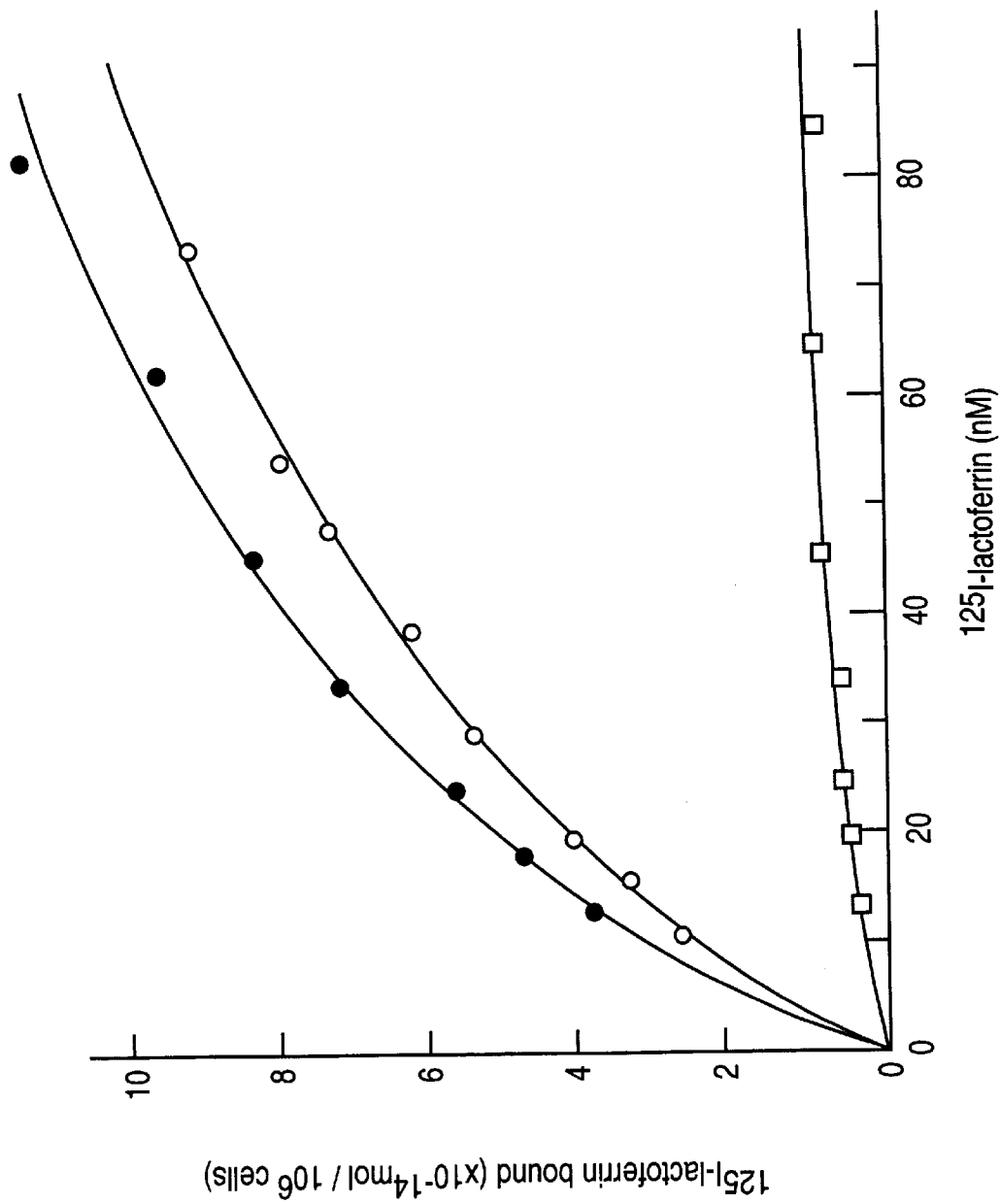
FIG. 9 shows binding of hLf, bLf and mLf to Jurkat cells as a function of concentration. Curves correspond to the specific binding of hLf (●); bLf(○) and mLf(□) to the cells. Values are means of two to three separate experiments in duplicate.
Figure 10A:
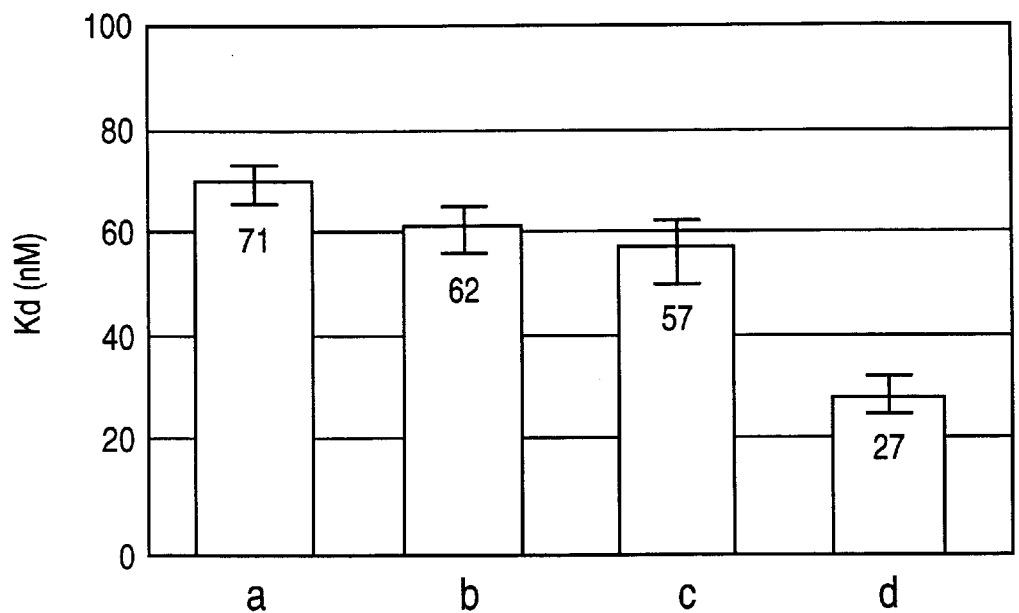
FIGS. 10A and 10B show binding parameters of hLf, bLf and mLf to Jurkat cells Dissociation constants (FIG. 10A) and numbers of binding sites per cell (FIG. 10B) of hLf (1), bLf (2) and mLf (3). Values are means (±S.E.M.) of two to three separate experiments in duplicate.
Figure 10B:
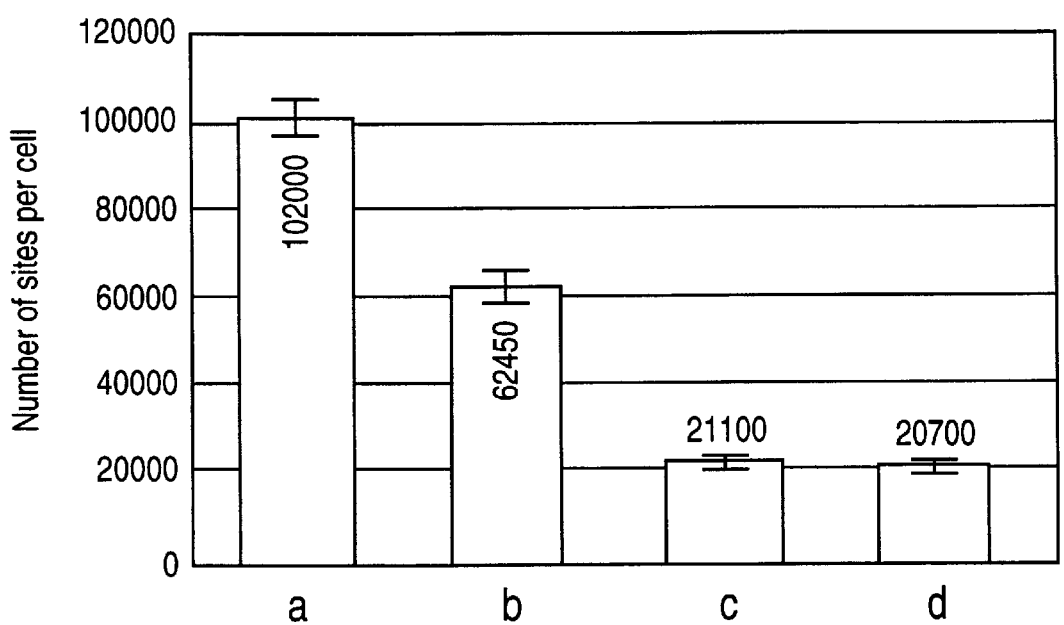
Figure 11:
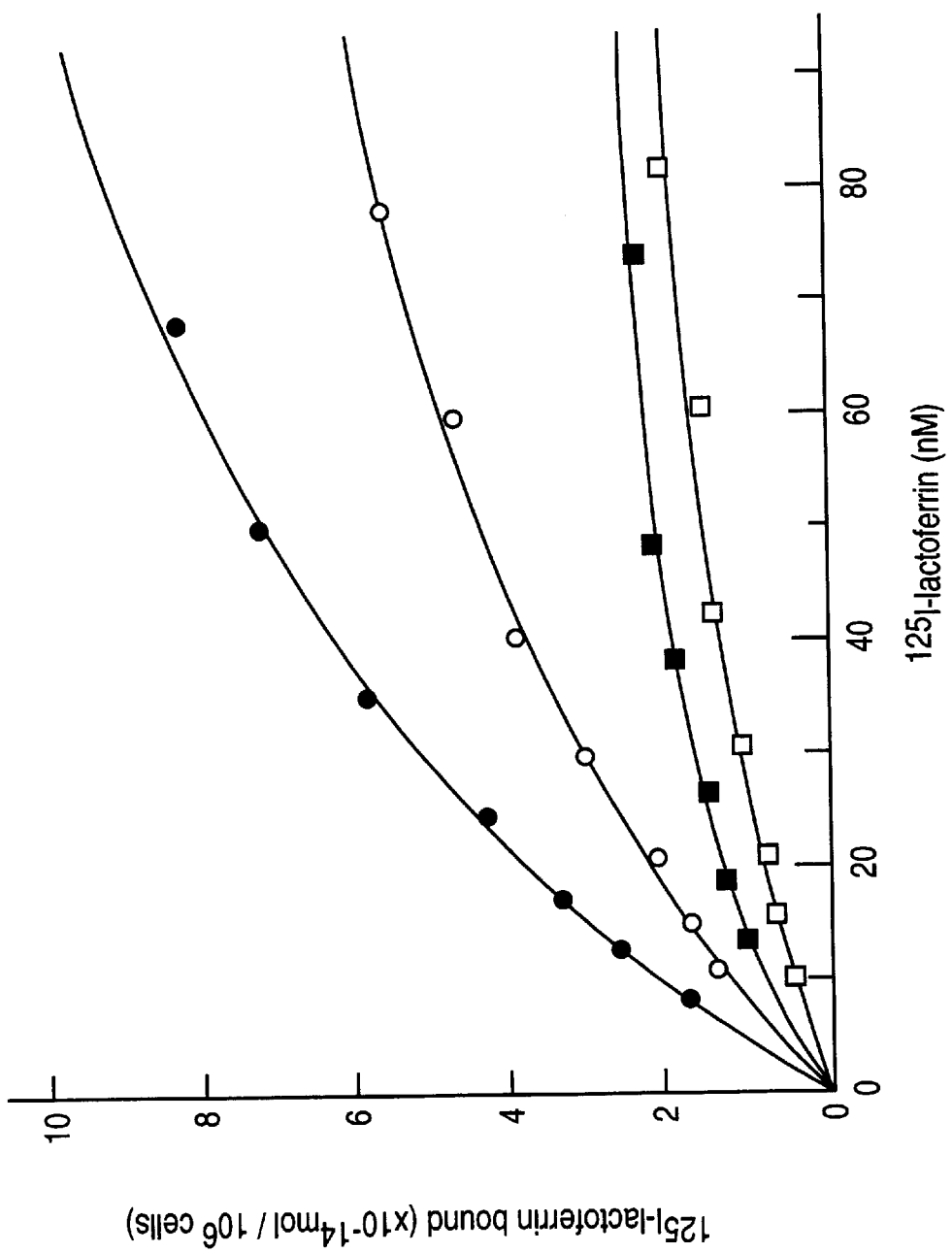
FIG. 11 shows the effect of the sodium chlorate treatment of Jurkat cells on the binding of native hLf and of N-terminally deleted hLf variants. Curves correspond to the specific binding of hLf (●) to Jurkat cells cultured in the absence of sodium chlorate and of hLf (○); $hLf^{-3N}$ (■); $rhLf^{-5N}$ (□) to Jurkat cells cultured 24 hours in presence of 30 mM sodium chlorate (see methods). Values are means of two to three seperate experiments in duplicate.

In order to assess the species specificity of lactoferrin-Jurkat cell interactions, the binding of $^{125}$I-hLF, bLf and mLf was studied. FIG. 9 shows that the binding curve of bLf is comparable to the one of hLf. Accordingly, the calculated Kd and number of binding sites per cell did not significantly differ, i.e. around 60 nM and 100,000 sites/cell for both Lf specie (FIG. 11). On the other hand, mLf bound to about 8,000 binding sites per cell, with a Kd of 31 nM. These binding parameters of mLf are comparable to those obtained with hLf$^{-4N}$ or rhLf$^{-5N}$ (FIG. 8B).

Figure 12A:
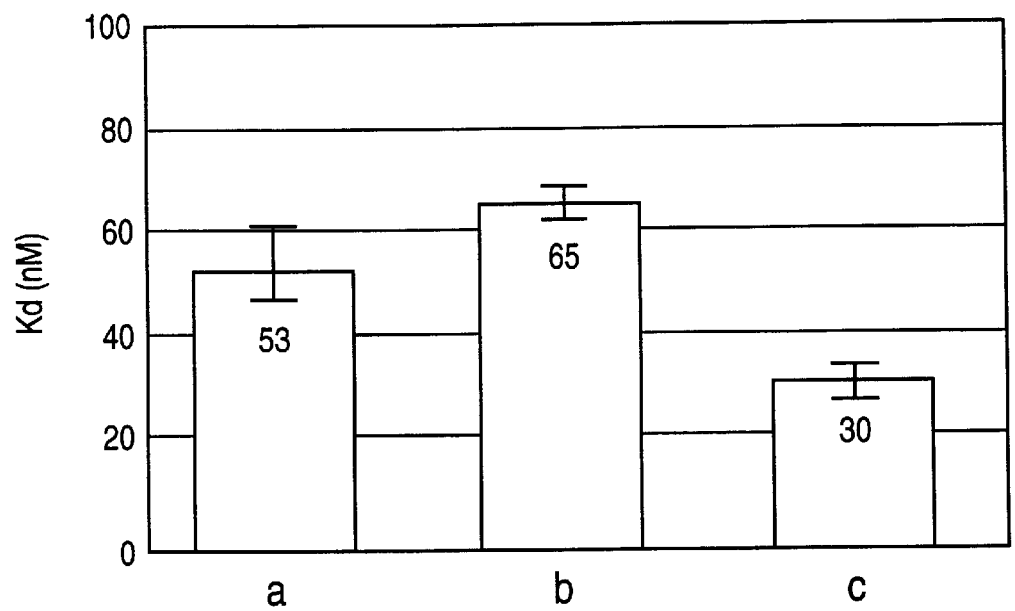
FIGS. 12A and 12B show shows the binding parameters of native hLf and of N-terminally deleted hLf variants to Jurkat cells cultured in presence or in absence of 30 mM sodium chlorate. Dissociation constants (FIG. 12A) and numbers of binding sites per cell (FIG. 12B) of hLf on cells cultured in absence of sodium chlorate (1) and of hLf (2); $hLf^{-3N}$ (3); $rhLf^{-5N}$ (4) on cells cultured in presence of sodium chlorate during 24 hours. Values are means (±S.E.M.) of two to three separate experiments in duplicate.
Figure 12B:
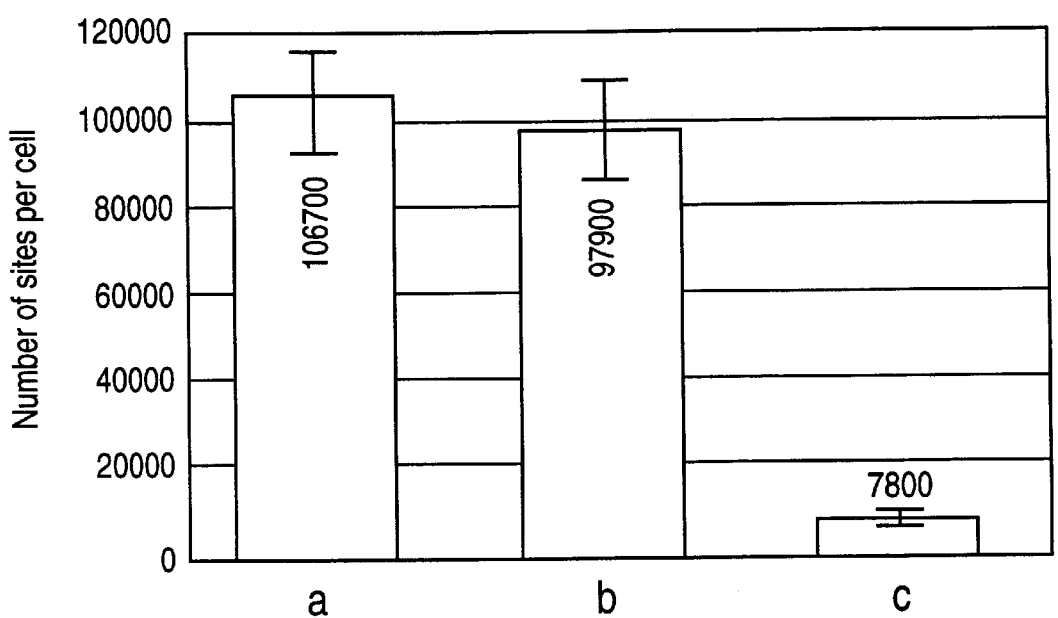

D. Effect of Sodium Chlorate Treatment on the Binding of hLf Species to Jurkat Cells To evaluate to which extent sulfated GAGs, such as heparin sulfate, dermatan sulfate or chondroitin sulfate, determine the binding of hLf to Jurkat cells, these cells were pretreated with sodium chlorate. Chlorate is an inhibitor of ATP sulfurylase and hence of the production of phosphoadenosine phosphosulfate, the active sulfate donor for sulfotransferases. Chlorate has been shown to abolish sulfation of carbohydrate residues on intact cells without interfering with cell growth or protein synthesis [22,23]. Jurkat cells were divided into two pools grown either in the absence or in the presence of 30 mM sodium chlorate for 24 h. Chlorate had no effect on either the growth rate nor on the morphology of Jurkat cells. Cells were washed and incubated with concentrations ranging from 0 to 80 nM of $^{125}$I-hLf, hLf$^{-3N}$ and rhLf$^{-5N}$. FIGS. 11 and 12 show that treatment of Jurkat cells with chlorate affected the binding parameters for native hLf. The Kd slightly decreased from 71.1 to 62.6 nM upon chlorate treatment and the amount of binding sites decreased from 102,000 to 65,450 per cell. Depletion of cell-associated sulfate groups resulted in a similar number of 21,000 binding sites recognizing either hLf$^{-3N}$ or rhLf$^{-5N}$ with Kd values of 57.2 and 27.9 nM, respectively (FIG. 11 and 12). This number of binding sites is very close to that found in untreated cells for both hLf$^{-4N}$ and rhLf$^{-5N}$ (around 17,000 sites/cell; FIGS. 8A and 8B). Thus, chlorate treatment decreased the number of binding sites of hLf$^{-3N}$ from 35,600 to 21,100, suggesting that hLf$^{-3N}$, but not rhLf$^{-5N}$, is still able to interact with sulfated groups exposed on the cell surface of untreated Jurkat cells.

III. Discussion

This example demonstrates the role of Arg$^2$-Arg$^3$-Arg$^4$-Arg$^5$ (SEQ ID NO:1) of hLf in the binding of this protein to the lymphoblastic cell line Jurkat.

Limited tryptic proteolysis of native hLf yields large amounts of N-terminally deleted hLf variants lacking either Gly$^1$-Arg$^2$, Gly$^1$-Arg$^2$-Arg$^3$ or Gly$^1$-Arg$^2$-Arg$^3$-Arg$^4$ (SEQ ID NO:14). The results of Table 3 show that cleavage after Arg$^2$ occurs before cleavage after Arg$^3$. Subsequent cleavage of the peptide bond after Arg$^4$, yielding hLf$^{-4N}$ occurs at a much slower rate. SDS-PAGE analysis showed that, under the mild hydrolysis conditions used, proteolysis had occurred mainly at the N-terminus. Inner tryptic proteolysis after Lys$^{283}$ was noted only in less than 3% of total hLf molecules after 3 h of digestion, whereas 2, 49 and 42% of the molecules lacked 4, 3 and 2 N-terminal residues, respectively. These results clearly demonstrate that tryptic proteolysis of the N-terminus occurs before cleavage after the major tryptic cleavage site at Lys$^{283}$. It is thus likely that degradation of the N-termiinus of hLf is easily achieved in external secretions, questioning the physiological significance of this process.

The binding parameters of native hLf to Jurkat cells were close to those previously described [34], whereas subsequent removal of one of the N-terminal arginines resulted in a progressive increase in affinity, as well as in a decrease in the number of the binding sites per cell. These results indicate that Arg$^2$, Arg$^3$ and to a lower extent, Arg$^4$ of hLf are synergistically involved in the binding of hLf to 'low affinity' binding sites on Jurkat cells representing about 80% of total binding. Removal of Arg$^5$ from hLf strongly increased the affinity of hLf for about 20,000 'high affinity' binding sites on Jurkat cells (FIGS. 8A and 8B) presumably representing the Lf specific receptor. It is thus likely that Arg$^5$ provides steric hindrance for the hLf lymphocytic receptor to reach the second basic cluster (Arg$^{28}$-Lys$^{29}$-Val$^{30}$-Arg$^{31}$ (SEQ ID NO:13), a region that was previously identified as part of the lactoferrin receptor binding site [21]. This would also explain why Arg$^5$ cannot be released from hLf following trypsin treatment. X-ray crystallographic data of hLf [20] indeed indicates that Arg$^5$ is linked to the protein core through a hydrogen bond. Arg$^5$ is thus likely more involved in the structural integrity of hLf than in interactions of hLf with other molecules. Taken together, these results indicate that Arg$^2$, Arg$^3$ and Arg$^4$ but not Arg$^5$ are synergistically required for the binding of hLf to about 80,000 low affinity binding sites at the surface of Jurkat cells. In addition, Jurkat cells contain about 20,000 high-affinity binding sites (Kd around 20 nM), which presumably represent the hLf receptor previously characterized [35]. Binding of hLf to this class of high-affinity binding sites does not require the presence of the first basic cluster.

These results suggest that Arg$^2$, Arg$^3$ and Arg$^4$ but not Arg$^5$ contribute to the recognition of proteoglycans on Jurkat cells.

The N-terminal cluster of four consecutive arginine residues is unique to hLf (FIG. 13) [36, 32]. Nevertheless, binding of bLf and hLf to Jurkat cells was comparable. Murine Lf exhibited only high affinity binding to a much lower number of binding sites (about 10,000 per cell), which is comparable to the binding parameters of hLf$^{-4N}$ and rhLf$^{-5N}$. This suggests that, in contrast to hLf and bLf, mLf did not interact with the Jurkat cell sulfated molecules but only with the lymphocyte receptor. Indeed, the N-terminal sequence of mLf differs from the hLf sequence (FIG. 13) as it contains only one lysine residue at position 1, providing a structural basis for the lack of proteoglycan interaction of mLf. Bovine Lf contains an Arg and a Lys residue at the homologous positions of Arg$^4$ and Arg$^5$ of hLf. The similar binding of both Lf species to Jurkat cells indicates that other basic residues in the N-terminus of bLf interact with proteoglycans. In terms of basic charges, it is worth noting that both hLf and bLf contain a similar number of 9 basic amino acids at different positions between residues 1 to 37, whereas mLf only contains 5 basic residues. Moreover, mLf possesses 4 Glu residues in the 1 to 37 region instead of 1 in hLf and bLf.

In conclusion, these data indicate that Arg$^2$-Arg$^3$-Arg$^4$ of hLf participate in the binding of the protein to lymphocytes. The first basic cluster of hLf was shown to interact with about 80,000 low-affmity binding sites which were mainly identified as sulfated cell surface molecules. Only about 20,000 high-affinity binding sites are likely to correspond to the hLf lymphocyte receptor previously characterized [35]. The quantitative preparation of N-terminally deleted hLf variants described herein offers the opportunity to gain further insight into the biological role of different binding sites expressed at the surface of lymphocytic cells.

References

1. Nuijens et al. (1996). Structure and biological actions of lactoferrin. *Journal of Mammary Gland Biologie and Neoplasia* 1: 285–295
2. Rey et al (1990). Complete nucleotide sequence of human mammary gland lactoferrin. *Nucleic Acids Res.* 18: 5288

3. H. F. Wu, R. L. Lundblad, and F. C. Church. (1995). Neutralization of heparin activity by neutrophil lactoferrin. *Blood* 85: 421–428
4. D. Wang, K. M. Pabst, Y. Aida, and M. J. Pabst. (1995). Lipopolysaccharide-inactivating activity of neutrophils is due to lactoferrin. *J. Leukoc. Biol.* 57: 865–874
5. P. H. C. Van Berkel, M. E. J. Geerts, H. A. van Veen, P. M. Kooiman, F. Pieper, H. A. de Boer, and J. H. Nuijens. (1995). Glycosylated and unglycosylated human lactoferrins can both bind iron and have identical affinities towards human lysozyme and bacterial lipopolysaccharide, but differ in their susceptibility towards tryptic proteolysis. *Biochem. J.* 312: 107–114
6. R. T. Ellison III, and T. J. Giehl. (1991). Killing of gram-negative bacteria by lactoferrin and lysozyme. *J. Clin. Invest.* 88: 1080–1091
7. J. H. Nuijens, C. C. M. Huijbregts, G. M. Van Mierlo, and C. E. Hack. (1987). Inactivation of C1 inhibitor by proteases: demonstration by a monoclonal antibody of a neodeterminant on inactivated, non-complexed C1 inhibitor. *Immunology* 61: 387–389
8. G. Köhler, and C. Milstein. (1975). *Nature (London)* 256: 495–497
9. P. H. C. Van Berkel, H. A. van Veen, M. E. J. Geerts, H. A. de Boer, and J. H. Nuijens. (1996). Heterogeneity in utalization of N-glycosylation sites Asn624 and Asn138 in human lactoferrn: study with glycosylation site mutants. *Biochem. J.* 319: 117–122
10. D. Koczan, G. Hobom, and H. M. Seyfert. (1991). Genomic organization of the bovine aS1 casein gene. *Nucleic Acids Res.* 19: 5591–5596
11. E. Elasg-Rochard, A. Roseanu, D. Legrand, M. Trif, V. Salmon, C. Motao, J. Montreuil, and G. Spik. (1995). Lactoferrin-lipopolysaccharide interactions: involvement of the 28–34 loop region of human lactoferrin in the high-affinity binding of *Eschericia coli* 055B5 lipopolysaccharide, *Biochem. J.* 312: 839–846
12. M. Gerstein, B. F. Anderson, G. E. Norris, E. N. Baker, A. M. Lesk, and C. Chothia (1993). Domain closure in lactoferrin. Two hinges produce a see-saw motion between alternative close-packed interfaces. *J. Mol. Biol.* 234: 357–372
13. M. Paulsson, Å. Ljungh, and T. Wadström. (1994). Inhibition of lactoferrin and vitronectin binding to *Staphylococcus aureus* by heparin. *Current Microbiol.* 29: 113–117
14. H. Shau, A. Kim, and S. H. Golub. (1992). Modulation of natural killer and lymphokine-activated killer cell cytotoxicity by lactoferrin. *J. Leukoc. Biol.* 51: 343–349
15. M. Meilinger, M. Haumer, K. A. Szakmary, F. Steinbock, B. Scheiber, H. Goldenberg, and M. Huettinger. (1995). Removal of lactoferrin from plasma is mediated by binding to low density lipoprotein receptor-related protein/alpha 2-macroglobulin receptor and transport to endosomes. *FEBS Lett.* 360: 70–74
16. G. J. Ziere, M. K. Bijsterbosch, and T. J. van Berkel. (1993). Removal of 14 N-terminal amino acids of lactoferrin enhances its affinity for parenchymal liver cells and potentiates the inhibition of beta- very low density lipoprotein binding. *J. Biol. Chem.* 268: 27069–27075
17. Mikogami, T., Heyman, M., Spik, G. and Desjeux, J. F. (1994) Am. J. Physiol. 267, G308–G315
18. van Berkel, P. H. C., Geerts, M. E., van Veen, H. A., Kooiman, P. M., Pieper, F. R., de Boer, H. A. and Nuijens, J. H. (1995) Biochem. J., 312, 107–114
19. Rey, M. W., Woloshuk, S. L., De Boer, H. A. and Pieper, F. R. (1990) Nucleic Acids Res. 18, 5288
20. Anderson, B. F., Baker, H. M., Norris, G. E., Rice, D. W. and Baker, E. N. (1989) J. Mol. Biol. 209, 711–734
21. Legrand, D., Mazurier, J., Elass, A., Rochard, E., Vergoten, G., Maes, P., Montreuil, J. and Spik, G. (1992) Biochemistry 31, 9243–9251
22. Baeuerle, P. A. and Huttner, W. B. (1986) Biochem. Biophys. Res. Commun. 141, 870–877
23. Keller, K. M., Brauer, P. R. and Keller, J. M. (1989) Biochemistry 28, 8100–8107
24. Spik, G., Strecker, G., Foumet, B., Bouquelet, S., Montreuil, J., Dorland, L., van Halbeek, H., Vliegenthart, J. F. G. (1982) Eur. J. Biochem. 121, 413–419
25. Laemmnli, U. K. (1970) Nature (London) 227, 680–685
26. Mazurier, J. and Spik, G. (1980) Biochim.Biophys. Acta 629, 399–409
27. Salmon, V., Legrand, D., Georges, B., Slomianny, M.-C., Coddeville, B. and Spik, G. (1996) Protein Expression and Purification—in press
28. Legrand, D., Salmon, V., Coddeville, B., Benaissa, M., Plancke, Y. and Spik, G. (1995) FEBS Lett. 365, 57–60
29. Scatchard, G. (1949) Ann. N.Y. Acad. Sci. 51, 660–672.
30. Legrand, D., Mazurier, J., Metz-Boutigue, M. H., Jollès, J., Jollès, P., Montreuil, J. and Spik, G. (1984) Biochim. Biophys. Acta 787,90–96.
31. Hutchens, T. W, Henry, J. P. and Yip, T. T. (1991) Proc. Natl. Acad. Sci. USA 88:2994–2998
32. Z. Y. Qian, P. Jolles, S. D. Migliore, and A. M. Fiat. (1995). Isolation and characterization of sheep lactofeirin, an inhibitor of platelet aggregation and comparison with human lactoferrin. *Biochim. Biophys. Acta* 1243: 25–32
33. H. E. Broxmeyer, D. E. Williams, G. Hangoc, S. Cooper, P. Gentile, R. N. Shen, P. Ralph, S. Gillis, and D. C. Bicknell. (1987). The opposing actions in vivo on murine myelopoiesis of purified preparations of lactoferrin and the colony stimulating factors. *Blood Cells* 13: 31–48 35.
34. Bi, B. Y., Liu, J. L., Legrand, D., Roche, A. C., Capron, M., Spik, G. and Mazurier, J. (1996) Eur. J. Cell Biol. 69,288–296
35. Mazurier, J., Legrand, D., Hu, W. L., Montreuil, J. and Spik, G. (1989) Eur. J. Biochem. 179,481487
36. Metz-Boutigue, M. H., Jollès, J., Mazurier, J., Schoentgen, F., Legrand, D., Spik, G., Montreuil, J. and Jollès, P. (1984) Eur. J. Biochem. 145, 659–676.

Example 3

This experiment describes the neutralization of heparin anticoagulant activity by human lactoferrin in vitro.

I. Introduction

The anti-inflammatory activity of drugs may be analyzed using a WB (whole-blood) assay in which anticoagulated blood is diluted ten times in endotoxin-free medium and transferred to 96 well plates. The effects of the addition of pro-inflammatory mediators such as lipopolysaccharides (LPS) from Gram-negative bacteria, immune complexes, or cytokines in the presence or absence of putative anti-inflammatory compounds, can be studied by measuring activation of plasma cascade systems (e.g., complement activation, thrombin-antithrombin III complex [TAT] for activation of the coagulation system, and/or monocyte cytokine production and activation of neutrophils). Lactoferrin binds with high affinity to the lipid A moiety of LPS, which is a strong mediator of inflammation. To investigate putative physiological consequences of lactoferrin binding to LPS, a series of experiments was conducted with lactofernn in the WB-assay. Significant differences in the effects of lactoferrin on pro-inflammatory cytokine production were noted when WB was performed in heparinized blood or in WB anticoagulated with TFPI (tissue-factor pathway inhibitor). It has been demonstrated that human lactoferrin binds to heparin (van Berkel et al. Biochem. J. 328, 145–151 (1997), Wu et al. Arch. Biochem. Biophys. 317, 85–92 (1995), Mann et al. J. Biol. Chem. 269, 23661–23667 (1994)), This interaction results in the neutralization of heparin activity in vitro (Wu et, Blood 85, 421–428 (1995)). The ability of lactoferrin to inhibit the anticoagulant activity of heparin was determined by measuring the amount of TAT complexes in whole blood cultures that were anticoagulated in the presence or absence of lactoferrin.

II. Methods

A. Protocol

Fresh human blood was diluted 10 times in culture medium (IMDM, Biowithaker) and anticoagulated with various concentrations of heparin (Leo, Leo Weesp) in the presence or absence of 100 μg/mnl lactoferrin. Wells were incubated for 2 h at 37° C. Samples were taken from supernatant and the amount of TAT complexes was determined by ELISA.

B. Proteins

Natural hLF (Batch 67), transgenic hLF, bovine lactoferrin, and commercially available batch Serva hLF (Feinbiochemica, Heidelberg) were used. $hLF^{-3N}$ (lacking $Gly^1$-$Arg^2$-$Arg^3$) was isolated from Serva hLF ((Feinbiochemica, Heidelberg).

III. Results

Figure 14:
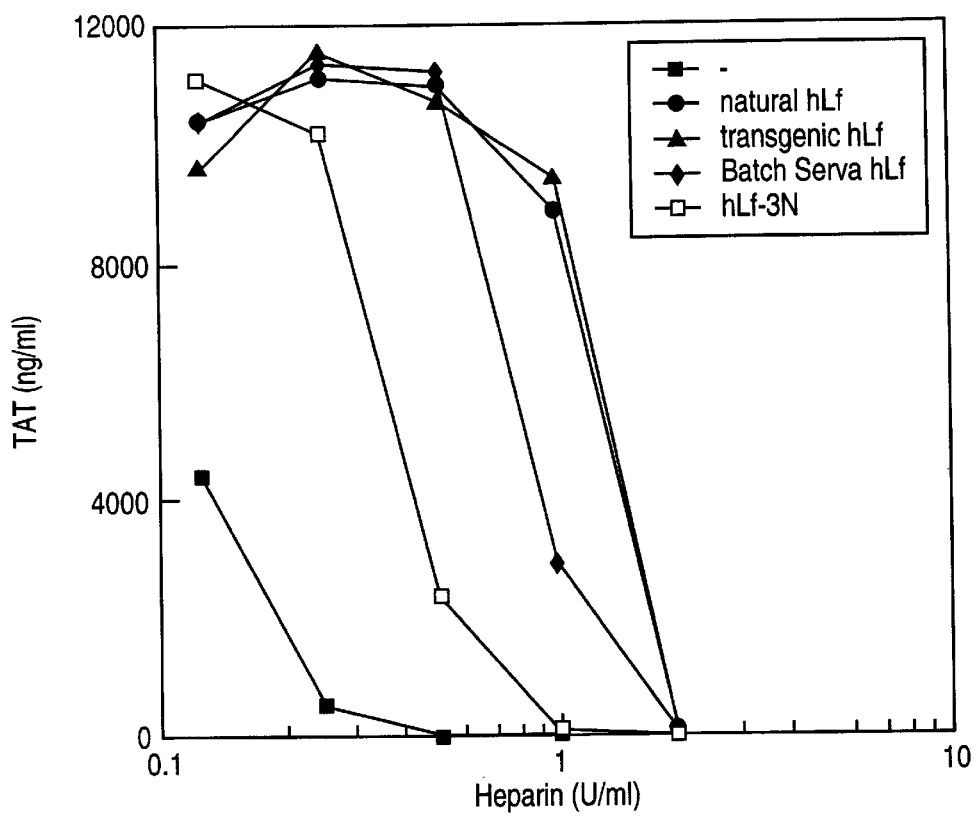
FIG. 14 shows neutralization of heparin by various lactoferrin species in whole blood cultures. Heparin at various concentrations was added to diluted whole blood in the presence or absence of 100 μg/ml lactoferrin. After 2 h, the amount of TAT complexes in supernatant were determined by ELISA.

The results with various lactoferrin species are shown in FIG. 14. In the presence of 100 μg/ml hLF, about 10 times more hepalin has to be added in order to obtain fully anticoagulated blood (TAT values <20 ng/ml). Similar curves are obtained with transgenic hLF from a bovine and genomic transgenic hLF from mice, indicating that they neutralize heparin equally well. $hLF^{-3N}$ binds to heparin with an eight-fold lower affinity when compared to N-terminal intact hLF. It neutralized heparin 2.1 and 3.5 fold less effective than Peak III of Serva and natural hLF, respectively. The relative reduced effect obtained using cDNA transgenic hLF from mice is likely due to the presence of large amounts of polybrene in this preparation.

Figure 15:
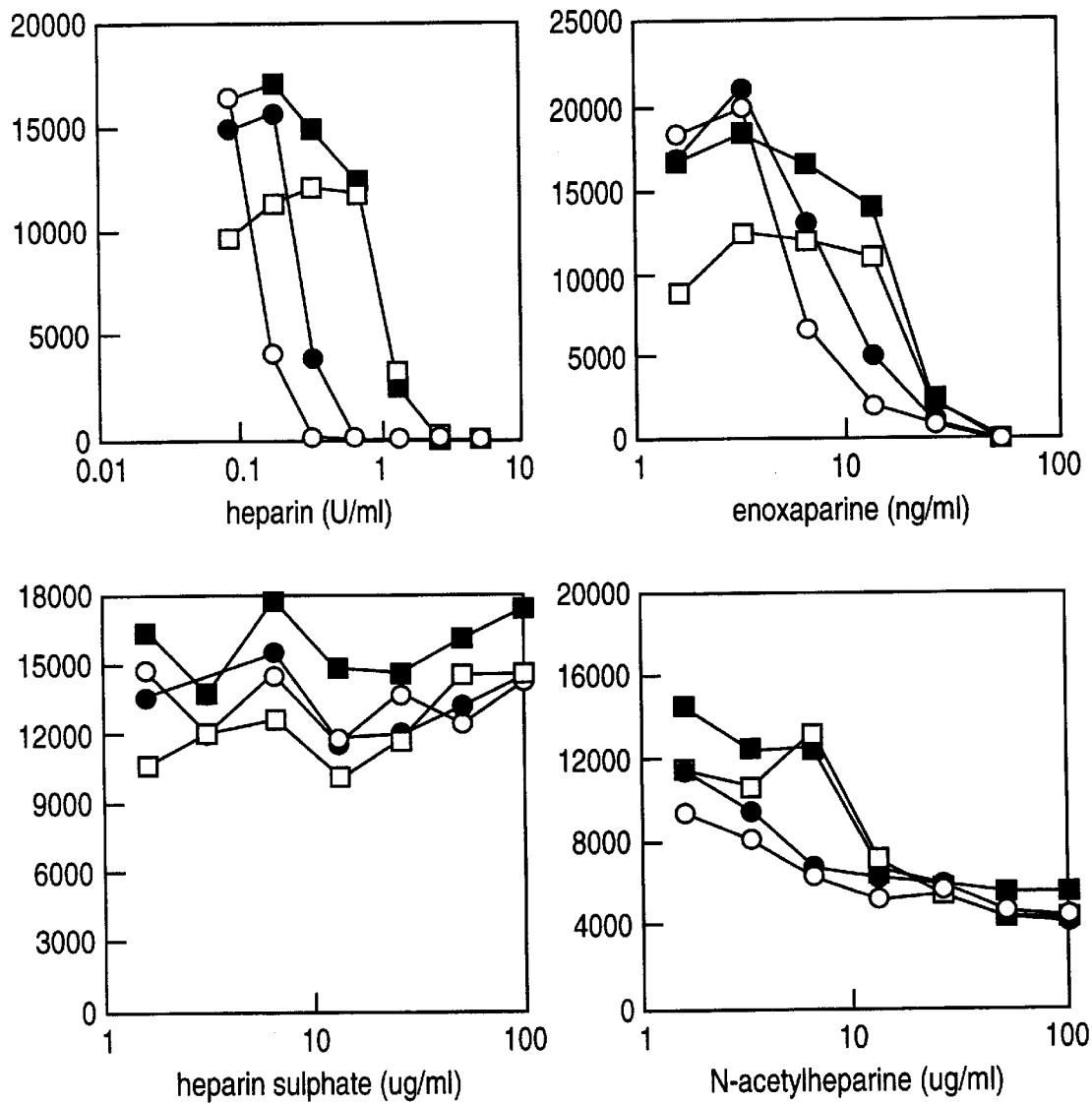
FIG. 15 shows anticoagulation of whole blood cultures by various GAGs and neutralization by lactofenin and protamine sulphate. Various concentrations of heparin, enoxaparine, heparan sulphate or N-acetylheparine were added to diluted whole blood in the absence (○) or presence of 100 μg/ml hLF (■), bLF (□), or 2 μg/ml protamine sulfate (●). After 2 h, the amount of TAT complexes in supernatant were determined by ELISA.

The ability of bovine lactoferrin (bLF), human lactoferrin and protamine sulfate to neutralize different glycosaminoglycans (heparin, enoxaparine, heparan sulphate and N-acetylheparine) was also determined. FIG. 15 shows that hLF and bLF equally well neutralize heparine and enoxaparine (which is a low-molecular weight heparin). Whole blood cultures with heparan sulphate and N-acetylheparine give rise to a fair amount of TAT indicating that these are not useful for anticoagulating whole blood. There is no effect of either hLF, bLF or protamine sulphate on heparan sulphate. Minor neutralization of N-acetylheparine by hLF and bLF was observed.

IV. Conclusions

The results supra suggest that:

1) Human and bovine lactoferrin also neutralize enoxaparine, which is a defined low-molecular weight heparin.

2) There seems to be no differences between different polymorphic $Arg^{29}/Lys^{29}$ variants (hLF batch 67 is heterozygous $Arg^{29}/Lys^{29}$, genomic transgenic hLF is homozygous $Arg^{29}/Arg^{29}$).

3) N-terminally degraded hLF ($hLF^{-3N}$) neutralizes heparin 2.1 and 3.5-fold lower, when compared to Peak III Serva hLF and natural hLF (box 67), respectively.

Example 4

This experiment describes binding characteristics of natural hLF, N-terminally degraded hLF variants, and iron-saturated hLF.

I. Introduction

Despite the small amount of iron in milk, an average of 49% of iron in breast milk is absorbed. This level is high compared to 10 to 12% from unfortified cow's milk and cow's milk formula. To explain the bioavailability of iron from human milk, the potential effect of human lactoferrin (hLF) on iron-absorption has long been proposed (Montreuil et al. Biochim. Biophys. Aeta 45, 413421 (1960)). In 1979, Cox et al., using pieces of human duodenal mucosa and $^{59}Fe$ labeled hLF fragments, provided evidence of an iron uptake process from hLF (Cox et al. Biochim. Biophys. Actu 588, 120–128 (1979)). This uptake process appeared to be species and protein specific, since uptake from bovine lactoferrin (bLF) was several fold reduced and no uptake was observed from human transferring and hen ovatransferrin. Following these findings, the presence of intact hLF in the feces of breast-fed infants reinforced the idea that hLF can escape from proteolytic attack during passage through the gastrointestinal tract and hLF may be involved in iron-absorption (Spik et al. Acta Pediatr. Scand. 71, 979–985 (1982)).

As described supra we identified the presence of two classes of hLF binding sites on lymphocytes (see also Legrand et Biochem. J. 327 841–846 (1997)). One class shows low-affinity binding of hLF and a high number of binding sites, whereas the second class shows high affnity binding and a low number of binding sites per cell (supra, Legrand et Biochem. J. 327 841–846 (1997)). Binding studies with natural and recombinant hLF variants revealed that the first basic cluster of hLF interacts with the low-affinity binding sites (presumably cell-associated proteoglycans). The second basic cluster of cationic residues in the hLF N-terminus is involved in the high affinity interaction with the putative hLF receptor on lymphocytes. Thus, the presence of two classes of hLF binding sites on intestinal cells may explain the binding charactristics of hLF to intestinal cells previously observed. In this experiment we have compared the binding parameters of N-terninally intact hLF to those of N-terminally degraded hLF variants. Furthermore, binding of iron-saturated hLF, bLF, mLF and transgenic hLF from cows was analyzed.

II. Methods

A. Binding Assay

Cells from human colon carcinoma cell line HT-29 (Mikogami et al. Am. J. Physiol. 267, G308–G315(1994)) were prepared and stored frozen. Cells were subcultured weekly and seeded at $2 \times 10^4$ cells/$cm^2$ (in 24 well plates) in DMEM containing 10% FCS for 3 weeks to reach a well differentiated state. The medium was changed daily. 220 μg of lactoferrin was radio labeled with $^{125}I$ using Iodo-gen. Cells were rinsed three times with cold DPBS. Incubation media were prepared in DPBS+(1 mM $Ca^{2+}$, 0.5 mM $Mg^{2+}$) containing 4.3 mg/ml apotransfernin plus lactoferrin (at varying concentrations) and added to the wells. Nonspecific binding was determined in the presence of a 100-fold molar excess of cold native hLF. After incubation for 1 h at 4° C., 50 µl of incubation media was collected and radioactivity was determined in Gamma counter. After removing the media, cells were rinsed five times with DPBS, harvested in DPBS-EDTA and cell-associated radioactivity was determined. Every concentration of lactoferrin was studied in duplicate at least three times.

B. Proteins

Natural human lactoferrin, iron-saturated hLF, transgenic hLF isolated from milk of a transgenic bovine, bovine lactoferrin, mouse lactoferrin, and N-terminally deleted hLf were used. Human lactoferrin lacking $Gly^1$-$Arg^2$ ($hLF^{-2N}$), $Gly^1$-$Arg^2$-$Arg^3$ ($hLF^{-3N}$) or $Gly^1$-$Arg^2$-$Arg^3$-$Arg^4$ (SEQ ID NO:14) ($hLF^{-4N}$) was produced by limited protealysis (described supra).

III. Results

Figure 16:
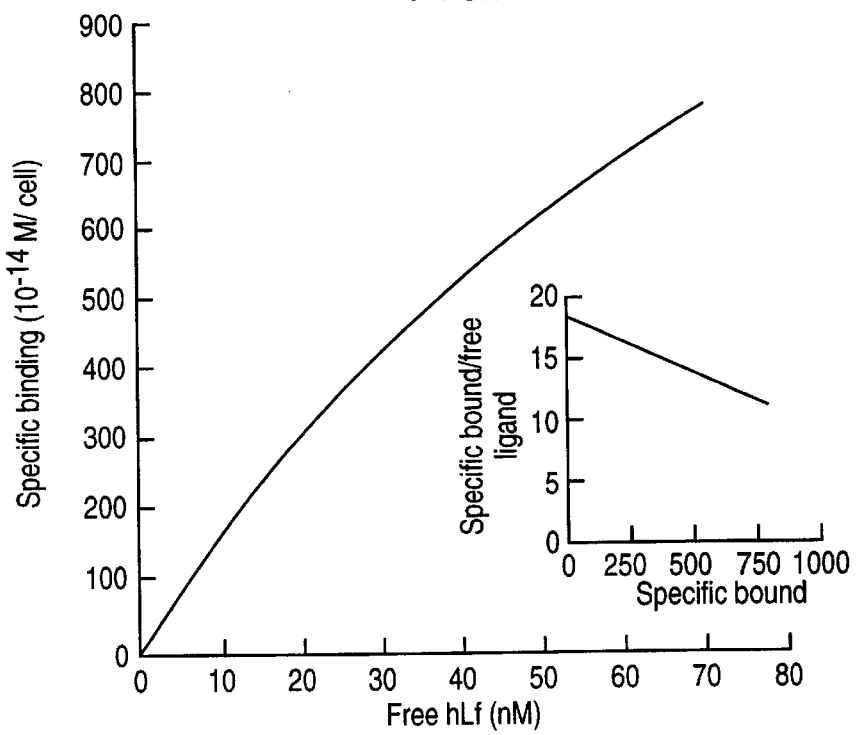
FIG. 16 shows specific binding of natural hLF to HT-29 cells. Values are the mean of a duplicate experiment. the inset shows a Scatchard analysis of the data.
Figure 17:
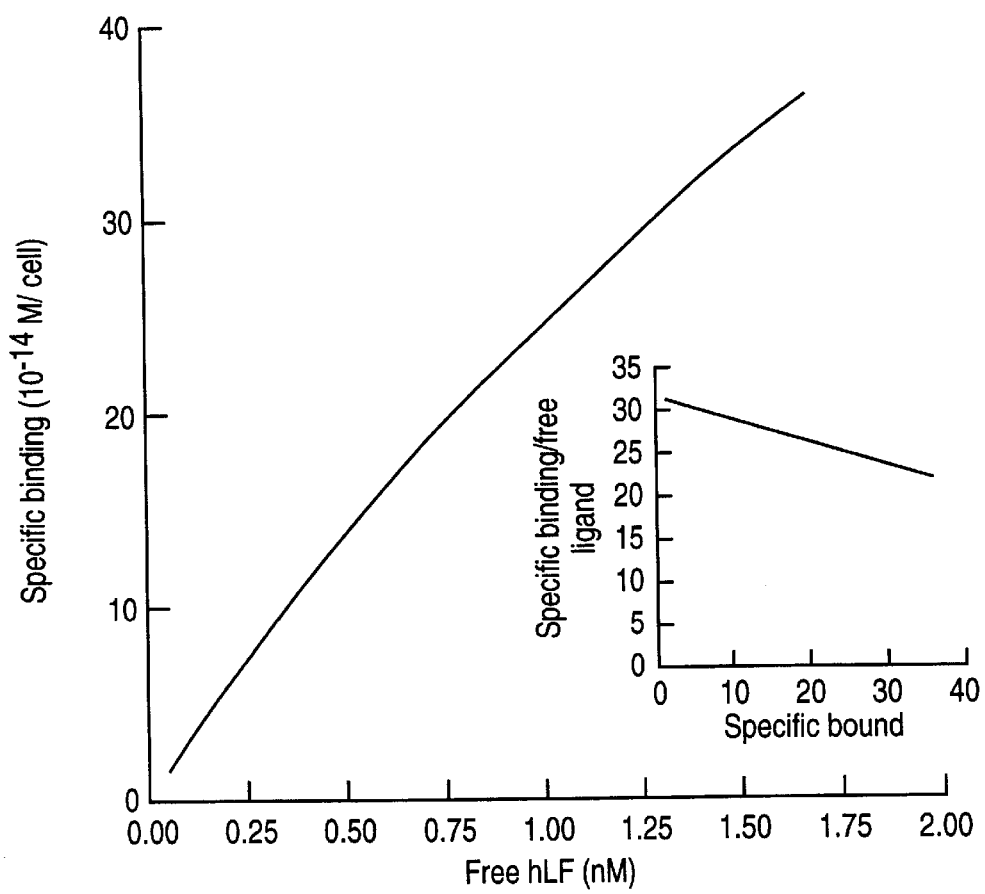
FIG. 17 shows specific high-annnity binding of natural hLF to HT-29 cells. Values are the mean of a duplicate experiment. The inlet shows a Scatchard analysis of the data.

FIG. 16 shows the binding of natural hLF to HT-29 cells. The figure depicts the specific binding of hLF, being the total binding minus non-specific binding (in the presence of a 100-fold molar excess of cold hLF). Within the concentrations tested, binding was relatively non-saturable. Scatchard analysis (inset) revealed that within these concentrations, hLF bound to $3.19 \times 10^6$ sites per cell with a dissociation constant of 1.1 µM. FIG. 17 shows the binding curve of lower hLF concentrations. Scatchard analysis of these data (inset of FIG. 17) revealed the presence of binding with higher affinity (36 nM) to $2.3 \times 10^5$ sites per cell. Similar experiments were performed with other lactoferrins and variants as summarized in Table 4. In every experiment natural hLF was included as a control. The binding parameters are divided into total binding and high-affinity binding. The results indicate that there is no difference in binding parameters between natural hLP, iron-saturated hLF, bovine lactoferrin and transgenic hLF from a transgenic bovine. Mouse lactoferrin does not bind to HT-29 cells. Removal of one N-terminal arginine has a minor impact on the binding parameters, although the affnity for the high affinity site decreases to a mean value of 124 nM. After removal of two Nterminal arginines, high affinity binding was lost. Although measured only once, the same is observed with hLF lacking three N-terminal arginines. These results differ from binding studies of N-terminally deleted hLF variant to Jurkat cells, where removal of N-terminal arginines decreases the number of binding sites per cell but increases the affinity. These results suggest that there is no specific receptor on HT-29, but only massive capacity binding to HT-29.

TABLE 4

Binding parameters of various lactoferrin species to HT-29 cells. The relatively large standard variation is related to the use of adherent cells (well to well variation).

|  | Total binding sites ($(10^6)$) | High Affinity sites ($(10^5)$) | Total affinity (µM) | High affinity (nM) | N |
|---|---|---|---|---|---|
| Natural hLF | 3.9 ± 1.5 | 3.3 ± 1.9 | 1.0 ± 0.5 | 74 ± 30 | 14 |
| Fe-hLF | 3.2 ± 0.3 | 2.6 ± 2.5 | 1.0 ± 0.3 | 66 ± 40 | 3 |
| Trans. hLF | 2.7 ± 0.7 | 4.6 ± 3.5 | 0.9 ± 0.6 | 88 ± 45 | 3 |
| bLF | 2.9 ± 1.3 | 3.5 ± 0.7 | 0.8 ± 0.5 | 81 ± 24 | 3 |
| mLF | — | — | — | — | 3 |
| $hLF^{-2N}$ | 5.6 ± 0.6 | 9.3 ± 4.4[a] | 0.8 ± 0.1 | 124 ± 8[a] | 3 |
| $hLF^{-3N}$ | 6.1 ± 1.5 | — | 1.7 ± 0.3 | — | 3 |
| $hLF^{-4N}$ | 8.9 | — | 0.7 | — | 1 |

[a]significantly different from natural hLF (P < 0.01).
N = number of independent experiments.

Figure 18:
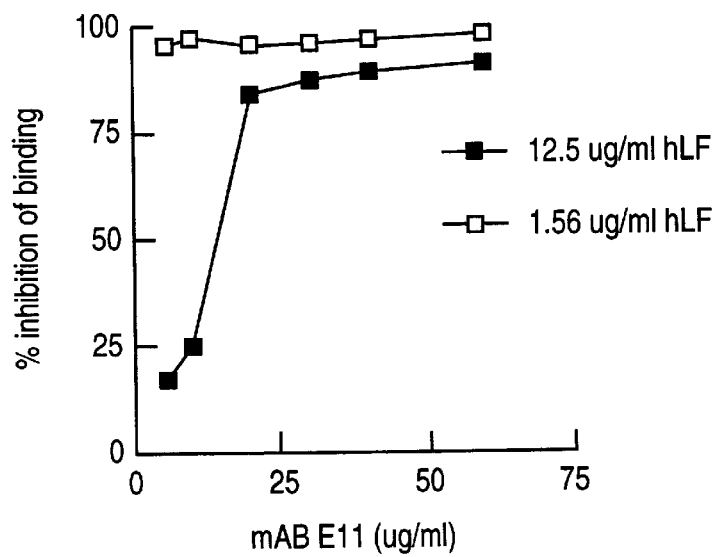
FIG. 18 shows inhibition of the binding of hLF to HT-29 cells. Human lactoferrin was preincubated for 1 h in the presence of increasing concentrations of mAb E11.

The observation that removal of N-terminal arginines abolishes binding to HT-29 cells suggests that binding to these sites is only mediated through the first basic cluster. To test this, the ability of monoclonal antibody mAb E11 to block binding of natural hLF to HT-29 cells was tested. This monoclonal antibody blocks binding of hLF to ligands like bacterial lipopolysaccharide, heparin (GAG) and was mapped to an epitope including $Arg^5$ (supra, van Berkel et al. *Biochem. J.* 328, 145–151 (1997)). FIG. 18 shows that a two-fold molar excess of E11 could completely block binding of hLF to HT-29. Scatcard analysis in the presence of 30 µg/ml hLF was indeed not possible due to total inhibition of The hLF binding (not shown). These results confirm that binding of hLF to HT-29 cells is solely mediated through the first basic cluster.

The effect of sodium chlorate on hLF binding to HT-29 cells was determined (as described supra for binding to Jurkat cells). Chlorate inhibits sulphation of carbohydrate residues on intact cells without interference with protein synthesis and treatment can be used to identify binding that relies on sulphated glycosarninoglycans (GAGs) such as heparan sulphate, dermatan sulphate or chondroitin sulphate. HT-29 cells were pretreated with 30 nM sodium chlorate for 24 in sulphate-free medium. Binding experiments were profound as described above. Preliminary results suggest that chlorate treatment has no significant effect on the binding parameters of human lactoferrin. Preliminary experiments were also performed with heparinase I. Cells were pretreated with 2.5 U/ml heparinase I in sulphate free medium for 4 h at 37° C. These preliminary results do not suggest that there is a difference between untreated and heparinase treated HT-29 cells.

IV. Conclusions

The results supra indicate that hLF binding to HT-29 cells is mediated entirely by the first basic cluster. This conclusion is based on the following results:

1) Removal of N-terminal arginines abolishes "high-affinity" binding of hLF to HT-29 cells.

2) The binding is completely blocked by anti-hLF mAb E11, which binds to an epitope that includes $Arg^5$ 3) Mouse lactoferrin, which lacks the entire first basic cluster, does not interact with HT-29 cells.

The results further suggest that there is no specific hLF-receptor expressed on HT-29. Binding to these cells solely occurs through as yet unidentified component(s). Possible candidates are glycosaminoglycans or sialic acids (on for instance mucins). It is thus not likely that a hLF-receptor mechanism is responsible for iron-uptake in the colon. Based on the results presented herein, these hLF variants will not bind to the intestinal wall and presumably be excreted.

For the purposes of clarity and understanding, the invention has been described in these examples and the above disclosure in some detail. It will be apparent, however, that certain changes and modifications may be practiced within the scope of the appended claims. All publications and patent applications are hereby incorporated by reference in their entirety for all purposes to the same extent as if each were so individually denoted.

What is claimed is:

1. A pharmaceutical composition comprising a human lactoferrin variant and a carrier, wherein the composition is substantially free of other human proteins, wherein the lactoferrin variant binds heparin with lower affinity than does natural lactoferrin, and wherein the human lactoferrin variant differs from human lactoferrin by a deletion or substitution of at least one arginine residue in the first basic cluster with an acidic or neutral amino acid residue.

2. A method for reducing the release of IL-1, IL-2, or TNFα from lactoferrin receptor-bearing cells in a patient, comprising administering to the patient a composition of claim 1, whereby release of IL-1, IL-2, or TNFα from lactoferrin receptor-bearing cells is reduced.

3. A method for delivering iron to a lactoferrin receptor-bearing cell in a patient, comprising administering to the patient a composition of claim 1, wherein the human lactoferrin is at least about 95% saturated with iron, whereby iron is delivered to a lactoferrin receptor-bearing cell.

4. A method for effecting a lactoferrin-mediated physiological change in a patient comprising administering to the patient a composition of claim 1, whereby a lactoferrin-mediated physiological change is effected, and wherein the physiological change is selected from the group consisting of inhibition of myelopoieses, reduction of TNFα-mediated neutrophil degranulation, reduction of anemia, increase of iron storage disease, reduction of inflammation, inhibition of growth of solid tumor, and stimulation of natural killer (NK) cells.

5. A pharmaceutical composition comprising a human lactoferrin variant and a carrier, wherein the composition is substantially free of other human proteins, wherein the lactoferrin variant binds heparin with lower affinity than does natural lactoferrin, and wherein the human lactoferrin variant is hLF-2N, hLF-3N, hLF-4N, or hLF-5N.

6. The composition of claim 5 further comprising bovine milk proteins.

7. The composition of claim 5 wherein the human lactoferrin variant is between about 3% and about 100% saturated with iron.

8. The composition of claim 7 wherein the human lactoferrin variant is at least about 95% saturated with iron.

9. A method for activating a lactoferrin receptor in a patient comprising administering the composition of claim 5.

10. The method of claim 9, wherein the lactoferrin receptor is a 105 kD lactoferrin receptor.

11. The method of claim 10 wherein the 105 kD receptor is a Jurkat cell lactoferrin receptor.

12. A method for reducing the release of IL-1, IL-2, or TNFα from lactoferrin receptor-bearing cells in a patient, comprising administering to the patient a composition of claim 5, whereby release of IL-1, IL-2, or TNFα from lactoferrin receptor-bearing cells is reduced.

13. A method for delivering iron to a lactoferrin-receptor-bearing cell in a patient, comprising administering to the patient a composition of claim 5, wherein the human lactoferrin is at least about 95% saturated with iron, whereby iron is delivered to a lactoferrin receptor-bearing cell.

14. A method for effecting a lactoferrin-mediated physiological change in a patient comprising administering to the patient a composition of claim 5, whereby a lactoferrin-mediated physiological change is effected, and wherein the physiological change is selected from the group consisting of inhibition of myelopoieses, reduction of TNFα-mediated neutrophil degranulation, reduction of anemia, increase of iron storage, reduction of inflammation, inhibition of growth of solid tumor, and stimulation of natural killer (NK) cells.

15. The method of claim 14 wherein said physiological change is inhibition of myelopoieses.

16. The method of claim 14 wherein said physiological change is reduction of TNFα-mediated neutrophil degranulation.

17. The method of claim 14 wherein said physiological change is reduction of anemia or increase of iron storage.

18. The method of claim 14 wherein said physiological change is reduction of inflammation.

19. The method of claim 14 wherein said physiological change is inhibition of growth of solid tumor.

20. The method of claim 14 wherein said physiological change is stimulation of natural killer (NK) cells.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Arg Arg Arg Arg
1

(2) INFORMATION FOR SEQ ID NO:2:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Arg Asn Met Arg Lys Val Arg
1               5

(2) INFORMATION FOR SEQ ID NO:3:

(i) SEQUENCE CHARACTERISTICS:
        (A) LENGTH: 52 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Gly Arg Arg Arg Arg Ser Val Gln Trp Cys Ala Val Ser Asn Pro Glu
1               5                  10                  15

Ala Thr Lys Cys Phe Gln Trp Gln Arg Asn Met Arg Lys Val Arg Gly
            20                  25                  30

Pro Pro Val Ser Cys Leu Lys Arg Asp Ser Pro Ile Gln Cys Ile Gln
        35                  40                  45

Ala Ile Ala Glu
    50

(2) INFORMATION FOR SEQ ID NO:4:

(i) SEQUENCE CHARACTERISTICS:
        (A) LENGTH: 51 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Ala Pro Arg Lys Asn Val Arg Trp Cys Thr Ile Ser Gln Pro Glu Trp
1               5                  10                  15

Phe Lys Cys Arg Arg Trp Gln Trp Arg Met Lys Leu Gly Ala Pro
            20                  25                  30

Ser Ile Thr Cys Val Arg Arg Ala Phe Ala Leu Glu Cys Ile Arg Ala
            35                  40                  45

Ile Ala Glu
    50

(2) INFORMATION FOR SEQ ID NO:5:

(i) SEQUENCE CHARACTERISTICS:
        (A) LENGTH: 50 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Lys Ala Thr Thr Val Arg Trp Cys Ala Val Ser Asn Ser Glu Glu Glu
 1               5                  10                  15

Lys Cys Leu Arg Trp Gln Asn Glu Met Arg Lys Val Gly Gly Pro Pro
            20                  25                  30

Leu Ser Cys Val Lys Lys Ser Ser Thr Arg Gln Cys Ile Gln Ala Ile
            35                  40                  45

Val Thr
    50

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Gly Arg Arg Arg Arg Ser Val Gln Trp Cys
 1               5                  10

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

CTGTTGCTCT TGCCAGTGTT CAGTGGTGC                                          29

(2) INFORMATION FOR SEQ ID NO:8:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Arg Arg Ala Arg
1
```

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
GGCCGTAGGA GAAGG                                          15
```

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

```
Gly Arg Arg Arg Arg
1               5
```

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

```
CTGTGTCTGG CTAGTGTTCA GTGGTG                              26
```

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

```
Ser Val Gln Trp Ala Cys Val
1               5
```

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

```
Arg Lys Val Arg
```

```
(2) INFORMATION FOR SEQ ID NO:14:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Gly Arg Arg Arg
```